(12) United States Patent
Kaumaya

(10) Patent No.: US 7,666,430 B2
(45) Date of Patent: Feb. 23, 2010

(54) POLYPEPTIDES AND POLYNUCLEOTIDES FOR ENHANCING IMMUNE REACTIVITY TO HER-2 PROTEIN

(75) Inventor: Pravin T. P. Kaumaya, Westerville, OH (US)

(73) Assignee: The Ohio State University, Columbus, OH (US)

( * ) Notice: Subject to any disclaimer, the term of this patent is extended or adjusted under 35 U.S.C. 154(b) by 16 days.

(21) Appl. No.: 11/423,194

(22) Filed: Jun. 9, 2006

(65) Prior Publication Data
US 2007/0071827 A1    Mar. 29, 2007

Related U.S. Application Data

(63) Continuation of application No. 09/632,036, filed on Aug. 3, 2000, now Pat. No. 7,060,284.

(60) Provisional application No. 60/146,869, filed on Aug. 3, 1999.

(51) Int. Cl.
*A61K 39/00* (2006.01)
*A61K 38/00* (2006.01)

(52) U.S. Cl. ............... 424/185.1; 424/277.1; 514/2; 514/13; 530/300; 530/326; 530/350

(58) Field of Classification Search ............ 530/300, 530/326, 350; 514/2, 13; 424/185.1, 277.1
See application file for complete search history.

(56) References Cited

U.S. PATENT DOCUMENTS

| | | | |
|---|---|---|---|
| 5,601,989 | A | 2/1997 | Cheever et al. |
| 5,726,023 | A | 3/1998 | Cheever et al. |
| 5,773,230 | A | 6/1998 | Cheever et al. |
| 5,801,005 | A | 9/1998 | Cheever et al. |
| 5,840,525 | A | 11/1998 | Vandlen et al. |
| 5,846,538 | A | 12/1998 | Cheever et al. |
| 5,869,445 | A | 2/1999 | Cheever et al. |
| 5,876,712 | A | 3/1999 | Cheever et al. |
| 6,015,567 | A | 1/2000 | Hudziak et al. |
| 6,075,122 | A | 6/2000 | Cheever et al. |
| 6,165,464 | A | 12/2000 | Hudziak et al. |
| 7,060,284 | B1 | 6/2006 | Kaumaya et al. |
| 2003/0170235 | A1 | 9/2003 | Cohen |
| 2004/0037823 | A9 | 2/2004 | Paton et al. |

FOREIGN PATENT DOCUMENTS

| | | |
|---|---|---|
| WO | 94/07531 | 4/1994 |
| WO | 97/38011 | 10/1997 |
| WO | 98/17797 | 4/1998 |
| WO | WO9931140 A1 * | 12/1999 |
| WO | 01/08636 | 2/2001 |

OTHER PUBLICATIONS

Bernards et al., "Effective tumor immunotherapy directed against an oncogene-encoded product using a vaccinia virus vector," Proc. Natl. Acad. Sci. USA (1987), vol. 84, No. 19, pp. 6854-6858.

Bowie et al., "Deciphering the message in protein sequences: tolerance to amino acid substitutions," Science, Mar. 16, 1990, vol. 247, No. 4948, pp. 1306-1310.

Dakappagari et al., Abstract P1012, "Evaluation of synergistic Interaction Between Cytokines and Peptide Epitope Vaccines in Protection Against HER-2 Expressing Lung Metastases," Second International and the Seventeenth American Peptide Symposium, Jun. 9-14, 2001, San Diego, California.

Dakappagari, "Evaluation of Chimeric B-Cell Epitope of HER-2: Application to Cancer Patients" Dissertation, The Ohio State University, submitted Jun. 1, 2001.

Dakappagari et al., "A Chimeric Multi-Human Epidermal Growth Factor Receptor-2 B Cell Epitope Peptide Vaccine Mediates Superior Antitumor Responses," The Journal of Immunology, Apr. 15, 2003, vol. 170, No. 8, pp. 4242-4253.

Dakappagari et al., "Conformational HER-2/neu B-cell epitope peptide vaccine designed to incorporate two native disulfide bonds enhances tumor cell binding and antitumor activities," J. Biol. Chem., Jan. 7, 2005, vol. 280, No. 1, pp. 54-63.

Dakappagari et al., "Prevention of Mammary Tumors with a Chimeric HER-2 B-cell Epitope Peptide Vaccine," Cancer Research, Jul. 15, 2000, vol. 60, pp. 3782-3789.

Dakappagari et al., Abstract P752, "Peptide Vaccine Strategies for Immunotherapy of HER-2/NEU Overexpressing Cancers," 16th American Peptide Symposium, Jun. 26-Jul. 1, 1999, Minneapolis, Minnesota.

Disis et al., "Granulocyte-Macrophage Colony Stimulating Factor: An effective Adjuvant for Protein and Peptide-Based Vaccines," Blood, Jul. 1, 1996, vol. 88, No. 1, pp. 202-210.

Disis et al., Immunization to Oncogenic HER-2/neu Protein with Peptide Based Vaccines, Proceedings of the Annual Meeting of the American Association for Cancer Research, New York, New York, Mar. 1995, vol. 36, p. 251.

Disis et al., "Peptide-Based, but not whole protein, vaccines elicit immunity HER-2/neu, an Oncogenic Self-Protein," J. of Immunol. (1996), vol. 56, pp. 3151-3158.

Frangione-Beebe et al., "Enhanced immunogenicity of a conformational epitope of human T-lymphotropic virus type 1 using a novel chimeric peptide," Vaccine (2001), vol. 19, pp. 1068-1081.

Gu et al., "A novel hydrophobized polysaccharide/oncoprotein complex vaccine induces in vitro and in vivo cellular and humoral immune responses against HER2-expressing murine sarcomas," Cancer Res. (1988), vol. 58, No. 15, pp. 3385-3390.

Guy et al., "Expression of the neu protooncogene in the mammary epithelium of transgenic mice induces metastatic disease," Proc. Natl. Acad. Sci. USA (1992), vol. 89, pp. 10578-10582.

(Continued)

*Primary Examiner*—Stephen L Rawlings
(74) *Attorney, Agent, or Firm*—Calfee, Halter & Griswold LLP

(57) ABSTRACT

Compositions for stimulating the immune system and for treating malignancies associated with overexpression of the HER-2 protein are provided. Such compositions include immunogenic epitopes of the HER-2 proteins and chimeric and multivalent peptides which comprise such epitopes. The present invention also relates to polynucleotides which encode the chimeric peptides. Also provided are pharmaceutical compositions comprising such immunogenic compositions. Methods for stimulating an immune response to HER-2 protein are provided. Methods for treating breast cancer, ovarian cancer, prostate cancer, colon cancer and lung cancer are provided.

19 Claims, 8 Drawing Sheets

OTHER PUBLICATIONS

Harwerth et al., "Monoclonal antibodies directed to the erbB-2 receptor inhibit in vivo tumour cell growth", Br. J. Cancer, Dec. 1993, vol. 68, No. 6, pp. 1140-1145.

Herrera et al., "Antigenicity and immunogenicity of multiple antigen peptides (MAP) containing P. vivax CS epitopes in Aotus monkeys," Parasite Immunology (1997), vol. 19, pp. 161-170.

Hopp et al., "Prediction of protein antigenic determinants from amino acid sequences," Proc. Natl. Acad. Sci. USA (1981), vol. 78, pp. 3824-3828.

Hudziak et al., "p185HER2 monoclonal antibody has antiproliferative effects in vitro and sensitizes human breast tumor cells to tumor necrosis factor," Mol. Cell. Biol. (1989), vol. 9, pp. 1165-1172.

Jiang et al., "Evaluation of the immunogenicity of peptide and DNA constructs for HER-2/neu epitopes," Peptides for the New Millennium, (Eds. Fields, G.B., Tam, T.P., and Barany), Kluwer Academic Publisher, Dordrecth, Netherlands, 2000, pp. 695-696.

Jiang et al., Abstract P751 "The Immunogenicity of Peptide Versus DNA Vaccine of an HER-2 CTL Epitope for Breast and Ovarian Cancers," 16th American Peptide Symposium, Jun. 26-Jul. 1, 1999, Minneapolis, Minnesota.

Kaumaya, "HER-2/neu Cancer Vaccines: Present Status and Future," International Journal of Peptide Research and Therapeutics (2006), vol. 12, No. 1, pp. 65-77.

Kaumaya et al., Abstract P1004, "A Combination of HER-2 Peptide Epitope Vaccines Mediate Superior Biological Effects," Second International and the Seventeenth American Peptide Symposium, Jun. 9-14, 2001, San Diego, California.

Kaumaya et al., "De Novo' Engineering of Peptide Immunogenic and Antigenic Determinants as Potential Vaccines," Peptides: Design, Synthesis and Biological Activity (1994), pp. 133-164.

Kaumaya et al., "Peptide Vaccines Incorporating a 'Promiscuous' T-cell Epitope bypass Certain Haplotype Restricted Immune Responses and Provide Broad Spectrum Immunogenicity," Journal of Molecular Recognition (1993) vol. 6, pp. 81-94.

Kawashima et al., "Identification of HLA-A3-restricted Cytotoxic T Lymphocyte Epitopes from Carcinoembryonic Antigen and HER-2/neu by Primary in Vitro Immunization with Peptide-pulsed Dendritic Cells," Cancer Research, Jan. 15, 1999, vol. 59, pp. 431-435.

Kelly et al., "T-Cell, Adhesion, and B-Cell Epitopes of the Cell Surface *Streptococcus mutans* Protein Antigen I/II," Infection and Immunity, Sep. 1995, vol. 63, No. 9, pp. 3649-3658.

Kono et al. "Identification of HER2/neu-Derived Peptide Epitopes Recognized by Gastric Cancer-Specific Cytotoxic T Lymphocytes," Int. J. Cancer (1998), vol. 78, pp. 202-208.

Kyngas et al., "Unreliability of the Chou-Fasman parameters in predicting protein secondary structure," Protein Eng. (1998), vol. 11, No. 5, pp. 345-348.

Lairmore et al., "Human T-Lymphotrophic Virus Type 1 Peptides in Chimeric and Multivalent Constructs with Promiscuous T-Cell Epitopes Enhance Immunogenicity and Overcome Genetic Restriction," Journal of Virology, Oct. 1995, vol. 69, No. 10, pp. 6077-6089.

Okugawa et al., "A novel human HER2-derived peptide homologous to the mouse K.sup.d-restricted tumor rejection antigen can induce HLA-A24-restricted cytotoxic T lymphyocytes in ovarian cancer patients and healthy individuals," Eur. J. Immunol (2000), vol. 30, pp. 3338-3346.

Pal et al. "β-Sheet propensity and its correlation with parameters based on conformation," Acta Crystallographica Section D, Biological Crystallography, May 2000, vol. 56, pp. 589-594.

Partidos et al., "Specificity of the T-cell responses in covalently linked peptides each comprising of a T helper epitope," Molecular Immunology (1997), vol. 34, No. 16-17, pp. 1105-1111.

Salazar et al., "Immunization of cancer patients with HER-2/neu-derived peptides demonstrating high-affinity binding to multiple class II alleles," Clinical Cancer Research, Nov. 15, 2003, vol. 9, pp. 5559-5565.

Schirle et al., "Combining computer algorithms with experimental approaches permits the rapid and accurate identification of T cell epitopes from defined antigens," Journal of Immunological Methods (2001), vol. 257, pp. 1-16.

Skolnick et al., "From genes to protein structure and function: novel applications of computational approaches in the genomic era," Trends Biotechnol., Jan. 2000, vol. 18, pp. 34-39.

Sotiriadou et al., "Peptide HER2(776-788) represents a naturally processed broad MHC class II-restricted T cell epitope," British Journal of Cancer (2001), vol. 85, No. 10, pp. 1527-1534.

Street et al., "Intrinsic β-sheet propensities result from van der Waals interactions between side chains and the local backbone," Proc. Natl. Acad. Sci. USA, Aug. 1999, vol. 96, pp. 9074-9076.

Thornton et al., "Location of 'continuous' antigenic determinants in the protruding regions of proteins," The EMBO Journal (1986), vol. 5, No. 2, pp. 409-413.

Triozzi et al., "Subunit Peptide Cancer Vaccines Targeting Activating Mutations of the p21 RAS Proto-Oncogene," Biomedical Peptides, Proteins and Nucleic Acids (1995), vol. 1, pp. 185-192.

Woodbine, "Biological Effects of Anti-Peptide Antibodies Against HER-2/NEU Receptor Tyrosine Kinase: Implications for Therapy of Human Breast Cancer" Dissertation, The Ohio State University, Submitted 1997, Published Aug. 5, 1998.

Woodbine et al., Abstract P442, "Biological Effects of Peptide Antibodies Raised to HER-2/neu. Implications for Therapy of Human Breast Cancer," The 1997 American Peptide Symposium, Jun. 14-19, 1997, Nashville, Tennessee.

Woodbine et al., Abstract MS009, "Peptide Vaccine Strategy for Immunotherapy of Human Breast Cancer Using HER-2/neu Oncogene," Fourteenth American Peptide Symposium, Jun. 18-23, 1995, Columbus, Ohio.

* cited by examiner

Cross Immunization – Basis for Multivalent Combination Vaccine

SEQUENCE LISTING

```
<160> NUMBER OF SEQ ID NOS: 45

<210> SEQ ID NO 1
<211> LENGTH: 19
<212> TYPE: PRT
<213> ORGANISM: Homo sapiens

<400> SEQUENCE: 1

Thr Gly Thr Asp Met Lys Leu Arg Leu Pro Ala Ser Pro Glu Thr His
1               5                   10                  15

Leu Asp Met

<210> SEQ ID NO 2
<211> LENGTH: 22
<212> TYPE: PRT
<213> ORGANISM: Homo sapiens

<400> SEQUENCE: 2

Ala Val Leu Asp Asn Gly Asp Pro Leu Asn Asn Thr Thr Pro Val Thr
1               5                   10                  15

Gly Ala Ser Pro Gly Gly
            20

<210> SEQ ID NO 3
<211> LENGTH: 22
<212> TYPE: PRT
<213> ORGANISM: Homo sapiens

<400> SEQUENCE: 3

Leu Trp Lys Asp Ile Phe His Lys Asn Asn Gln Leu Ala Leu Thr Leu
1               5                   10                  15

Ile Asp Thr Asn Arg Ser
            20

<210> SEQ ID NO 4
<211> LENGTH: 35
<212> TYPE: PRT
<213> ORGANISM: Homo sapiens

<400> SEQUENCE: 4

Thr Leu Ile Asp Thr Asn Arg Ser Arg Ala Cys His Pro Cys Ser Pro
1               5                   10                  15

Met Cys Lys Gly Ser Arg Cys Trp Gly Glu Ser Ser Glu Asp Cys Gln
            20                  25                  30

Ser Leu Thr
        35
```

```
<210> SEQ ID NO 5
<211> LENGTH: 21
<212> TYPE: PRT
<213> ORGANISM: Homo sapiens

<400> SEQUENCE: 5

Ala Leu Val Thr Tyr Asn Thr Asp Thr Phe Glu Ser Met Pro Asn Pro
1               5                   10                  15

Glu Gly Arg Tyr Thr
            20

<210> SEQ ID NO 6
<211> LENGTH: 24
<212> TYPE: PRT
<213> ORGANISM: Homo sapiens

<400> SEQUENCE: 6

Pro Leu His Asn Gln Glu Val Thr Ala Glu Asp Gly Thr Gln Arg Ala
1               5                   10                  15

Glu Lys Cys Ser Lys Pro Cys Ala
            20

<210> SEQ ID NO 7
<211> LENGTH: 18
<212> TYPE: PRT
<213> ORGANISM: Homo sapiens

<400> SEQUENCE: 7

Pro Glu Ser Phe Asp Gly Asp Pro Ala Ser Asn Thr Ala Pro Leu Gln
1               5                   10                  15

Pro Glu

<210> SEQ ID NO 8
<211> LENGTH: 20
<212> TYPE: PRT
<213> ORGANISM: Homo sapiens

<400> SEQUENCE: 8

Leu Tyr Ile Ser Ala Trp Pro Asp Ser Leu Pro Asp Leu Ser Val Phe
1               5                   10                  15

Gln Asn Leu Gln
            20

<210> SEQ ID NO 9
<211> LENGTH: 19
<212> TYPE: PRT
<213> ORGANISM: Homo sapiens

<400> SEQUENCE: 9

Leu Phe Arg Asn Pro His Gln Ala Leu Leu His Thr Ala Asn Arg Pro
1               5                   10                  15

Glu Asp Glu

<210> SEQ ID NO 10
<211> LENGTH: 34
<212> TYPE: PRT
<213> ORGANISM: Homo sapiens

<400> SEQUENCE: 10

Cys Leu Pro Cys His Pro Glu Cys Gln Pro Gln Asn Gly Ser Val Thr
1               5                   10                  15
```

```
Cys Phe Gly Pro Glu Ala Asp Gln Cys Val Ala Cys Ala His Tyr Lys
            20                  25                  30
Asp Pro

<210> SEQ ID NO 11
<211> LENGTH: 18
<212> TYPE: PRT
<213> ORGANISM: Homo sapiens

<400> SEQUENCE: 11

Lys Pro Asp Leu Ser Tyr Met Pro Ile Trp Lys Phe Pro Asp Glu Glu
1               5                   10                  15

Gly Ala

<210> SEQ ID NO 12
<211> LENGTH: 22
<212> TYPE: PRT
<213> ORGANISM: Homo sapiens

<400> SEQUENCE: 12

Ile Asn Gly Thr His Ser Cys Val Asp Leu Asp Asp Lys Gly Cys Pro
1               5                   10                  15

Ala Glu Gln Arg Ala Ser
            20

<210> SEQ ID NO 13
<211> LENGTH: 19
<212> TYPE: PRT
<213> ORGANISM: Clostridium tetani

<400> SEQUENCE: 13

Asn Ser Val Asp Asp Ala Leu Ile Asn Ser Thr Ile Tyr Ser Tyr Phe
1               5                   10                  15

Pro Ser Val

<210> SEQ ID NO 14
<211> LENGTH: 17
<212> TYPE: PRT
<213> ORGANISM: Clostridium tetani

<400> SEQUENCE: 14

Pro Gly Ile Asn Gly Lys Ala Ile His Leu Val Asn Asn Gln Ser Ser
1               5                   10                  15

Glu

<210> SEQ ID NO 15
<211> LENGTH: 15
<212> TYPE: PRT
<213> ORGANISM: Clostridium tetani

<400> SEQUENCE: 15

Gln Tyr Ile Lys Ala Asn Ser Lys Phe Ile Gly Ile Thr Glu Leu
1               5                   10                  15

<210> SEQ ID NO 16
<211> LENGTH: 21
<212> TYPE: PRT
<213> ORGANISM: Clostridium tetani

<400> SEQUENCE: 16

Phe Asn Asn Phe Thr Val Ser Phe Trp Leu Arg Val Pro Lys Val Ser
1               5                   10                  15
```

```
Ala Ser His Leu Glu
            20

<210> SEQ ID NO 17
<211> LENGTH: 15
<212> TYPE: PRT
<213> ORGANISM: Measles virus

<400> SEQUENCE: 17

Leu Ser Glu Ile Lys Gly Val Ile Val His Arg Leu Glu Gly Val
1               5                   10                  15

<210> SEQ ID NO 18
<211> LENGTH: 15
<212> TYPE: PRT
<213> ORGANISM: Hepatitis B virus

<400> SEQUENCE: 18

Phe Phe Leu Leu Thr Arg Ile Leu Thr Ile Pro Gln Ser Leu Asn
1               5                   10                  15

<210> SEQ ID NO 19
<211> LENGTH: 20
<212> TYPE: PRT
<213> ORGANISM: Plasmodium sp.

<400> SEQUENCE: 19

Thr Cys Gly Val Gly Val Arg Val Arg Ser Arg Val Asn Ala Ala Asn
1               5                   10                  15

Lys Lys Pro Glu
            20

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Pro Ser Leu
1

<210> SEQ ID NO 21
<211> LENGTH: 9
<212> TYPE: PRT
<213> ORGANISM: Homo sapiens

<400> SEQUENCE: 21

Ile Leu Trp Lys Asp Ile Phe His Lys
1               5

<210> SEQ ID NO 22
<211> LENGTH: 9
<212> TYPE: PRT
<213> ORGANISM: Homo sapiens

<400> SEQUENCE: 22

Ile Leu Lys Glu Thr Glu Leu Arg Lys
1               5

<210> SEQ ID NO 23
<211> LENGTH: 9
```

```
<212> TYPE: PRT
<213> ORGANISM: Homo sapiens

<400> SEQUENCE: 23

Val Leu Arg Glu Asn Thr Ser Pro Lys
1               5

<210> SEQ ID NO 24
<211> LENGTH: 9
<212> TYPE: PRT
<213> ORGANISM: Homo sapiens

<400> SEQUENCE: 24

Ala Ala Arg Pro Ala Gly Ala Thr Leu
1               5

<210> SEQ ID NO 25
<211> LENGTH: 9
<212> TYPE: PRT
<213> ORGANISM: Homo sapiens

<400> SEQUENCE: 25

Leu Pro Ala Ser Pro Glu Thr His Leu
1               5

<210> SEQ ID NO 26
<211> LENGTH: 9
<212> TYPE: PRT
<213> ORGANISM: Homo sapiens

<400> SEQUENCE: 26

Leu Pro Thr His Asp Pro Ser Pro Leu
1               5

<210> SEQ ID NO 27
<211> LENGTH: 9
<212> TYPE: PRT
<213> ORGANISM: Homo sapiens

<400> SEQUENCE: 27

Cys Arg Trp Gly Leu Leu Leu Ala Leu
1               5

<210> SEQ ID NO 28
<211> LENGTH: 9
<212> TYPE: PRT
<213> ORGANISM: Homo sapiens

<400> SEQUENCE: 28

Arg Arg Phe Thr His Gln Ser Asp Val
1               5

<210> SEQ ID NO 29
<211> LENGTH: 9
<212> TYPE: PRT
<213> ORGANISM: Homo sapiens

<400> SEQUENCE: 29

Gly Arg Ile Leu His Asn Gly Ala Tyr
1               5

<210> SEQ ID NO 30
<211> LENGTH: 9
<212> TYPE: PRT
<213> ORGANISM: Homo sapiens
```

```
<400> SEQUENCE: 30

Thr Tyr Leu Pro Thr Asn Ala Ser Leu
1               5

<210> SEQ ID NO 31
<211> LENGTH: 9
<212> TYPE: PRT
<213> ORGANISM: Homo sapiens

<400> SEQUENCE: 31

Glu Tyr Val Asn Ala Arg His Cys Leu
1               5

<210> SEQ ID NO 32
<211> LENGTH: 9
<212> TYPE: PRT
<213> ORGANISM: Homo sapiens

<400> SEQUENCE: 32

Ala Tyr Ser Leu Thr Leu Gln Gly Leu
1               5

<210> SEQ ID NO 33
<211> LENGTH: 9
<212> TYPE: PRT
<213> ORGANISM: Homo sapiens

<400> SEQUENCE: 33

Ala Leu Cys Arg Trp Gly Leu Leu Leu
1               5

<210> SEQ ID NO 34
<211> LENGTH: 8
<212> TYPE: PRT
<213> ORGANISM: Homo sapiens

<400> SEQUENCE: 34

His Leu Tyr Gln Gly Cys Gln Val
1               5

<210> SEQ ID NO 35
<211> LENGTH: 9
<212> TYPE: PRT
<213> ORGANISM: Homo sapiens

<400> SEQUENCE: 35

Gln Leu Arg Ser Leu Thr Glu Ile Leu
1               5

<210> SEQ ID NO 36
<211> LENGTH: 9
<212> TYPE: PRT
<213> ORGANISM: Homo sapiens

<400> SEQUENCE: 36

Ile Leu His Asn Gly Ala Tyr Ser Leu
1               5

<210> SEQ ID NO 37
<211> LENGTH: 9
<212> TYPE: PRT
<213> ORGANISM: Homo sapiens

<400> SEQUENCE: 37
```

```
Ile Leu Leu Val Val Val Leu Gly Val
1               5
```

<210> SEQ ID NO 38
<211> LENGTH: 9
<212> TYPE: PRT
<213> ORGANISM: Homo sapiens

<400> SEQUENCE: 38

```
Asp Leu Thr Ser Thr Val Gln Leu Val
1               5
```

<210> SEQ ID NO 39
<211> LENGTH: 9
<212> TYPE: PRT
<213> ORGANISM: Homo sapiens

<400> SEQUENCE: 39

```
Val Leu Val Lys Ser Pro Asn His Val
1               5
```

<210> SEQ ID NO 40
<211> LENGTH: 9
<212> TYPE: PRT
<213> ORGANISM: Homo sapiens

<400> SEQUENCE: 40

```
Lys Ile Phe Gly Ser Leu Ala Phe Leu
1               5
```

<210> SEQ ID NO 41
<211> LENGTH: 9
<212> TYPE: PRT
<213> ORGANISM: Homo sapiens

<400> SEQUENCE: 41

```
Ile Ile Ser Ala Val Val Gly Ile Leu
1               5
```

<210> SEQ ID NO 42
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Thr Gly Thr Asp Met Lys Leu Arg Leu Pro Ala Ser Pro Glu Thr His
1               5                   10                  15

Leu Asp Met Gly Pro Ser Leu Asn Ser Val Asp Asp Ala Leu Ile Asn
            20                  25                  30

Ser Thr Ile Tyr Ser Tyr Phe Pro Ser Val
        35                  40
```

<210> SEQ ID NO 43
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Pro Leu His Asn Gln Glu Val Thr Ala Glu Asp Gly Thr Gln Arg Ala
1               5                   10                  15

Glu Lys Cys Ser Lys Pro Cys Ala Gly Pro Ser Leu Asn Ser Val Asp
            20                  25                  30

Asp Ala Leu Ile Asn Ser Thr Ile Tyr Ser Tyr Phe Pro Ser Val
            35                  40                  45

<210> SEQ ID NO 44
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Leu Phe Arg Asn Pro His Gln Ala Leu Leu His Thr Ala Asn Arg Pro
1               5                   10                  15

Glu Asp Glu Gly Pro Ser Leu Asn Ser Val Asp Ala Leu Ile Asn
            20                  25                  30

Ser Thr Ile Tyr Ser Tyr Phe Pro Ser Val
            35                  40

<210> SEQ ID NO 45
<211> LENGTH: 24
<212> TYPE: PRT
<213> ORGANISM: Homo sapiens

<400> SEQUENCE: 45

Pro Leu His Asn Gln Glu Val Thr Ala Glu Asp Gly Thr Gln Arg Cys
1               5                   10                  15

Glu Lys Cys Ser Lys Pro Cys Ala
            20
```

POLYPEPTIDES AND POLYNUCLEOTIDES FOR ENHANCING IMMUNE REACTIVITY TO HER-2 PROTEIN

CROSS-REFERENCE TO RELATED APPLICATION

The present application is a Continuation of U.S. application Ser. No. 09/632,036, filed Aug. 3, 2000, which under 35 USC §119(e)(1) claims the benefit of prior U.S. provisional application 60/146,869, filed Aug. 3, 1999. The entire disclosures of application Ser. No. 09/632,036 and 60/146,869 are incorporated herein by reference.

The work described in this application was supported, at least in part, by grants PHS/NIH P30 CA-16058 and NIH/NCI ROI CA 84356-01A1 from the National Cancer Institute. The United States government has certain rights in this invention.

BACKGROUND

Currently, the most common forms of treating breast cancer involve surgery, chemical intervention, and/or radiotherapy. Unless the cancer is restricted to a defined area, surgery alone cannot eliminate the cancer. Accordingly, radiation treatment is often given after surgery to destroy cancer cells that are near the surgical site and that have evaded surgery. The side effects of such treatment include skin sensitivity or itchiness, interference with the immune system, sometimes queasiness and, rarely, radiation fibrosis where an affected portion of the lung becomes fibrous. Chemotherapy may also be employed following surgery. Chemotherapy utilizes drugs that are toxic to cancer cells. Since this is not a perfectly selective system, normal cells are affected as well. Negative side effects include nausea, tiredness, loss of appetite, hair loss and diarrhea.

In view of the disadvantages of the present therapies, attempts have been made to find additional approaches for treating breast cancer. One such approach is immunotherapy. One of the targets for an immunotherapeutic approach is the HER-2 protein. The HER-2 protein, a product of the HER-2 oncogene, is overexpressed in a variety of cancers. It is found in 50%-60% of ductal in situ carcinoma and 20%-40% of all breast cancers, as well as a substantial fraction of adenocarcinomas arising in the ovaries, prostate, colon and lung. Overexpression of the HER-2 protein is related to malignant transformation in humans. Overexpression of the HER-2 protein is also intimately associated with the aggressiveness of the malignancy, being found in one-fourth of all invasive breast cancers. Overexpression of HER-2 protein is correlated with a poor prognosis in both breast and ovarian cancer.

In recent studies, antibodies directed against the extracellular binding domain (ECD) of HER-2 have been shown to confer inhibitory effects on tumor growth in vitro and in animal models (Hudziak, R. M., et al., Mol. Cell. Biol., 9:11-65-72, 1989; Tagliabue, E., et al., Int. J. Cancer 47:933-7, 1991; Drebin, J. A., et al., Proc. Natil. Acad. Scie. USA 83:9129-33, 1986; Drebin, J. A., et al., Oncogene, 2:273-7, 1988; Drebin, J. A., et al., Oncogene, 2:387-94, 1988; and Katsumata, M., et al., Nat. Med. 1:644-8. 1995.) In addition, Phase II and III clinical trials of a recombinant humanized anti-HER-2 monoclonal antibody, Trastuzumab, in patients with metastatic, HER-2-overexpressing breast cancers produced an overall response rate of 15% as a single agent. Trastuzumab has also been shown to improve survival when combined with cytotoxic chemotherapeutics (Baselga, J., et al., J. Clin. Oncol. 14:737-44, 1996; Pegram, M. D., et al., J. Clin. Oncol., 16:2659<-71, 1988.). A number of vaccine approaches targeting a recombinant HER.-2 protein, the HER-2 ECD, or the ECD of rat neu, which is the rat homolog of HER-2 have also been evaluated. For example, strain NFS mice immunized with a vaccinia virus recombinant that expresses the ECD rat nue developed a protective antibody response against subsequent challenge with neu-transformed NIH 3T3 cells (Bernards, R., et al., Proc. Natl. Acad. Sci. USA, 84:6854-8, 1987.). Immunization of BDIX rats with the same immunogen, however, did not result in antibody response nor did it inhibit the growth of syngeneic neu-expressing B104 neuroblastoma cells, suggesting that this strategy was insufficient to induce immune responses in the rat. A polysaccharide-oncoprotein complex vaccine, consisting of the 147 amino-terminal amino acids of HER-2 ECD complexed with cholesteryl group-bearing mannan and pullulan, induced cellular and humoral immune responses that mediated rejection of HER-2-expressing sarcomas in BALB/c mice (Gu, X. G., et al., Cancer Res., 58: 3385-90, 1998.). Partial protection was shown in rat net transgenic mice destined to develop mammary tumors by immunizing with either a purified rat neu ECD (Esserman, L. J., Cancer Immunol. Immunother., 47:337-42, 1999.) or neu-transfected allogeneic mouse fibroblasts (Cefai, D., et al., Int. J. Cancer, 83:393-400, 1999.)

Despite the results of the studies described above, it is still uncertain whether effective immune responses can be generated in humans using cell-or protein-based vaccine strategies targeting HER-2 or the HER-2 ECD, as HER-2 is a non-mutated, "self" antigen. Accordingly, it is desirable to have additional immunotherapeutic approaches for treating or preventing breast cancer and other malignancies with which overexpression of the HER-2 protein is associated.

SUMMARY OF THE INVENTION

The present invention provides new compounds and compositions for stimulating the immune system and for treating malignancies associated with overexpression of the HER-2 protein. The compounds are immunogenic epitopes of the HER-2 protein, and chimeric and multivalent peptides which comprise such epitopes.

The first group of compounds are referred to hereinafter collectively as "HER-2 B cell epitopes." The HER-2 B cell epitopes comprise from about 15 to about 50 amino acids, more preferably from 17 to 40 amino acids, most preferably from 18 to 35 amino acids. Preferably, the HER-2 B cell epitope comprises a sequence selected from the following group or a functional equivalent thereof:

| | |
|---|---|
| TGTDMKLRLPASPETHLDM,; | SEQ ID NO. 1 |
| AVLDNGDPLNNTTPVTGASPGG,; | SEQ ID NO. 2 |
| LWKDIFHKNNQLALTLIDTNRS,; | SEQ ID NO. 3 |
| TLIDTNRSRACHPCSPMCKGSRCWGESSEDCQSLT,; | SEQ ID NO. 4 |
| ALVTYNTDTFESMPNPEGRYT,; | SEQ ID NO. 5 |
| PLHNQEVTAEDGTQRAEKCSKPCA,; | SEQ ID NO. 6 |
| PESFDGDPASNTAPLQPE,; | SEQ ID NO. 7 |
| LYISAWPDSLPDLSVFQNLQ,, | SEQ ID NO. 8 |
| LFRNPHQALLHTANRPEDE,; | SEQ ID NO. 9 |

```
-continued
CLPCHPECQPQNGSVTCFGPEADQCVACAHYKDP,;    SEQ ID NO. 10

KPDLSYMPIWKFPDEEGA,;                     SEQ ID NO. 11

INGTHSCVDLDDKGCPAEQRAS,.                 SEQ ID NO. 12
```

The HER-2 B cell epitopes listed above and their functional equivalents have the ability to induce production of antibodies which are immunoreactive with the extracellular domain of the HER-2 protein.

The present invention also provides chimeric peptides, referred to hereinafter as "chimeric HER-2 B cell peptides", which comprise at least one of the present HER-2 B cell epitopes or a functional equivalent thereof. Preferably the chimeric HER-2 B cell peptides are from about 35 to about 150, more preferably from about 35 to about 70 amino acids in length. The chimeric HER-2 B cell peptides comprise three units. The first unit comprises the HER-2 B cell epitope or functional equivalents thereof. The second unit is a helper T (Th) cell epitope, preferably a promiscuous Th cell epitope. As used herein a "promiscuous" Th cell epitope is one which promotes release of cytokines that assist in bypassing MHC restriction. The second unit is from about 14 to about 22, more preferably about 15 to 21, most preferably 16 amino acids in length. Preferably, the Th cell epitope has one of the following amino acid sequences:

N-S-V-D-D-A-L-I-N-S-T-J-Y-S-Y-F-P-S-V, SEQ ID NO. 13, referred to hereinafter as "TT";
P-G-I-N-G-K-A-I-H-L-V-N-N-Q-S-S-E, SEQ ID NO. 14, referred to hereinafter as "TT1";
Q-Y-I-K-A-N-S-K-F-I-G-I-T-E-L, SEQ ID NO. 15, referred to hereinafter as "P2";
F-N-N-F-T-V-S-F-W-L-R-V-P-K-V-S-A-S-H-L-E, SEQ ID NO. 16, referred to hereinafter as "P30";
L-S-E-I-K-G-V-I-V-H-R-L-E-G-V, SEQ ID NO. 17, referred to hereinafter as "MVF";
F-F-L-L-T-R-I-L-T-I-P-Q-S-L-N, SEQ ID NO. 18, referred to hereinafter as "HBV";
T-C-G-V-G-V-R-V-R-S-R-V-N-A-A-N-K-K.-P-E, SEQ ID NO. 19, referred to hereinafter as "CSP".

The third unit joins the first and second peptide units. The third unit is an amino acid or, preferably, a peptide of from about 2 to about 15 amino acids, more preferably from about 2 to about 10 amino acids, most preferably from about 2 to about 6 amino acids in length. The most preferred linker comprises the amino acid sequence Gly-Pro-Ser-Leu, SEQ ID NO. 20.

The present invention also provides multivalent HER-B cell peptides which comprise a plurality, i.e., at least two of the present HER 2-B cell epitopes or functional equivalents thereof and a Th cell epitope. The HER-2 B cell epitopes and Th cell epitope are connected to a core β sheet template. Preferably, the template comprises two strands of alternating leucine and lysine residues, which are connected by a linker. The linker is an amino acid or, preferably, a peptide of from about 2 to about 15 amino acids, more preferably from about 2 to about 10 amino acids, most preferably from about 2 to about 6 amino acids in length. The most preferred linker comprises the amino acid sequence Gly-Pro-Ser Leu, SEQ ID NO. 20.

The present invention also relates to an immunogenic composition containing the chimeric HER-2 B cell peptide or multivalent HER-2 B cell peptide and a pharmacologically acceptable carrier. The preferred carrier is a biodegradable microsphere. Such immunogenic compositions are useful for treating or preventing malignancies with which overexpression of the HER-2 protein is associated.

The present invention also relates to polynucleotides which encode at least one of the HER-2 B cell epitopes described above. Such polynucleotides are useful for producing the epitope by recombinant techniques. The present invention also relates to isolated polynucleotides having a sequence which encodes a chimeric HER-2 B cell peptide of the present invention. Such polynucleotides are useful for preparing the chimeric HER-2 B cell peptide. Such polynucleotides are also useful in an immunogenic composition (e.g., DNA vaccine) for treating or preventing malignancies in which overexpression of the HER-2 protein is associated. Preferably, such immunogenic compositions are administered intramuscularly.

The present invention also provides HER-2 epitopes which are capable of activating cytotoxic (Tc) cells, referred to hereinafter as "HER-2 CTL epitopes." The HER-2 CTL epitopes comprise from about 8 to about 12 amino acids, more preferably from 9 to 11 amino acids. Preferably, the HER-2 CTL epitope comprises one of the following sequences:

```
ILWKDIFHK,;      SEQ ID NO. 21
ILKETELRK,;      SEQ ID NO. 22
VLRENTSPK,;      SEQ ID NO. 23
AARPAGATL,;      SEQ ID NO. 24
LPASPETHL,;      SEQ ID NO. 25
LPTHDPSPL,;      SEQ ID NO. 26
CRWGLLLAL,;      SEQ ID NO. 27
RRFTHQSDV,;      SEQ ID NO. 28
GRILHNGAY,;      SEQ ID NO. 29
TYLPTNASL,;      SEQ ID NO. 30
EYVNARHCL,;      SEQ ID NO. 31
AYSLTLQGL,;      SEQ ID NO. 32
ALCRWGLLL,;      SEQ ID NO. 33
HLYQGCQV,;       SEQ ID NO. 34
QLRSLTEIL,;      SEQ ID NO. 35
ILHNGAYSL,;      SEQ ID NO. 36
ILLVVVLGV,;      SEQ ID NO. 37
DLTSTVQLV,;      SEQ ID NO. 38
VLVKSPNHV,;      SEQ ID NO. 39
KIFGSLAFL,;      SEQ ID NO. 40
IISAVVGIL,.      SEQ ID NO. 41
```

The present HER-2 CTL epitopes also encompass peptides that are functional equivalent of the HER-2 CTL epitopes shown above. The peptides which are functional equivalents have a sequence which is at least 90% identical to one of the sequences shown above. The peptides which are functional equivalents also have the ability to activate Tc cells.

The present invention also provides chimeric peptides, referred to hereinafter as chimeric HER-2 CTL peptides which comprise a HER-2 CTL epitopes or a functional equivalent thereof. The chimeric HER-2 CTL peptide comprises three units. The first unit comprises a CTL epitope. The second unit, preferably, is a promiscuous T helper cell epitope. The third unit is a linker amino acid or peptide unit which joins the first and second peptide units.

The present invention also provides multivalent HER-2 CTL peptides which comprise a plurality, i.e., at least two of the present HER 2 CTL epitopes or functional equivalents thereof and a Th cell epitope. The HER-2 CTL epitopes and Th cell epitope are connected to a core β sheet template. Preferably, the template comprises two strands of alternating leucine and lysine residues, which are joined by a linker.

The chimeric HER-2 CTL peptides and multivalent HER-2 CTL peptides are useful immunogens for activating Tc cells. Such activation induces the Tc cell to begin expressing the IL-2 receptor and to a lesser extent IL-2, the principal cytokine required for proliferation and differentiation of the activated Tc cell into a functional cytotoxic lymphocyte which possess cytotoxic activity against target cells that present the epitope. The present invention also relates to an immunogenic composition containing the chimeric HER-2 CTL peptide or multivalent HER-2 CTL peptide and a pharmacologically acceptable carrier. The present invention also relates to a method of activating Tc cells in a mammal by administering the immunogenic composition to such animal.

The present invention also encompasses isolated polynucleotides which encode one or more of the HER-2 CTL epitopes described above. Such polynucleotides are useful for producing the epitope by recombinant techniques. The present invention also encompasses isolated polynucleotides having a sequence which encodes a chimeric HER-2 CTL peptide. Such polynucleotides are useful for preparing the chimeric CTL cell epitope peptide. Such polynucleotides are also useful in an immunogenic composition, (e.g., DNA vaccine) for treating or preventing malignancies in which the HER-2 oncogene is associated.

The present invention also relates to a multivalent B/CTL peptide, which comprises one or more HER-2 B cell epitopes, linked to one or more HER-2 CTL epitopes linked to one or more T helper cell epitopes. The epitopes are linked to a core β sheet template. The present invention also relates to polynucleotides which encode multivalent B/CTL peptides and to DNA vectors that comprise such polynucleotides. The present invention also relates to an immunogenic composition comprising the B/CTL epitope peptide or polynucleotide encoding the same and a pharmaceutically acceptable carrier.

The present invention also relates to methods of stimulating an immune response in a subject to HER-2 protein. Such method comprises administering the chimeric or multivalent peptides of the present invention to the subject. Such method results in enhancement of the subject's immunity against a disease condition associated with expression of the HER-2 protein.

DETAILED DESCRIPTION OF THE INVENTION

Figure 1:
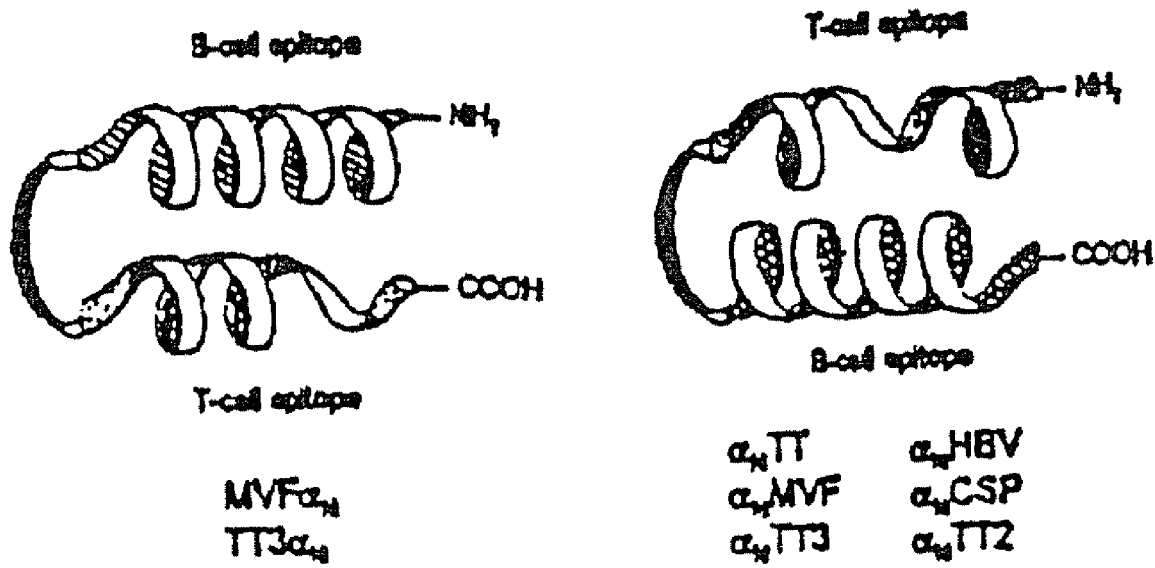
FIG. 1 is a schematic representation of a chimeric HER-2 B cell peptide.
Figure 2:
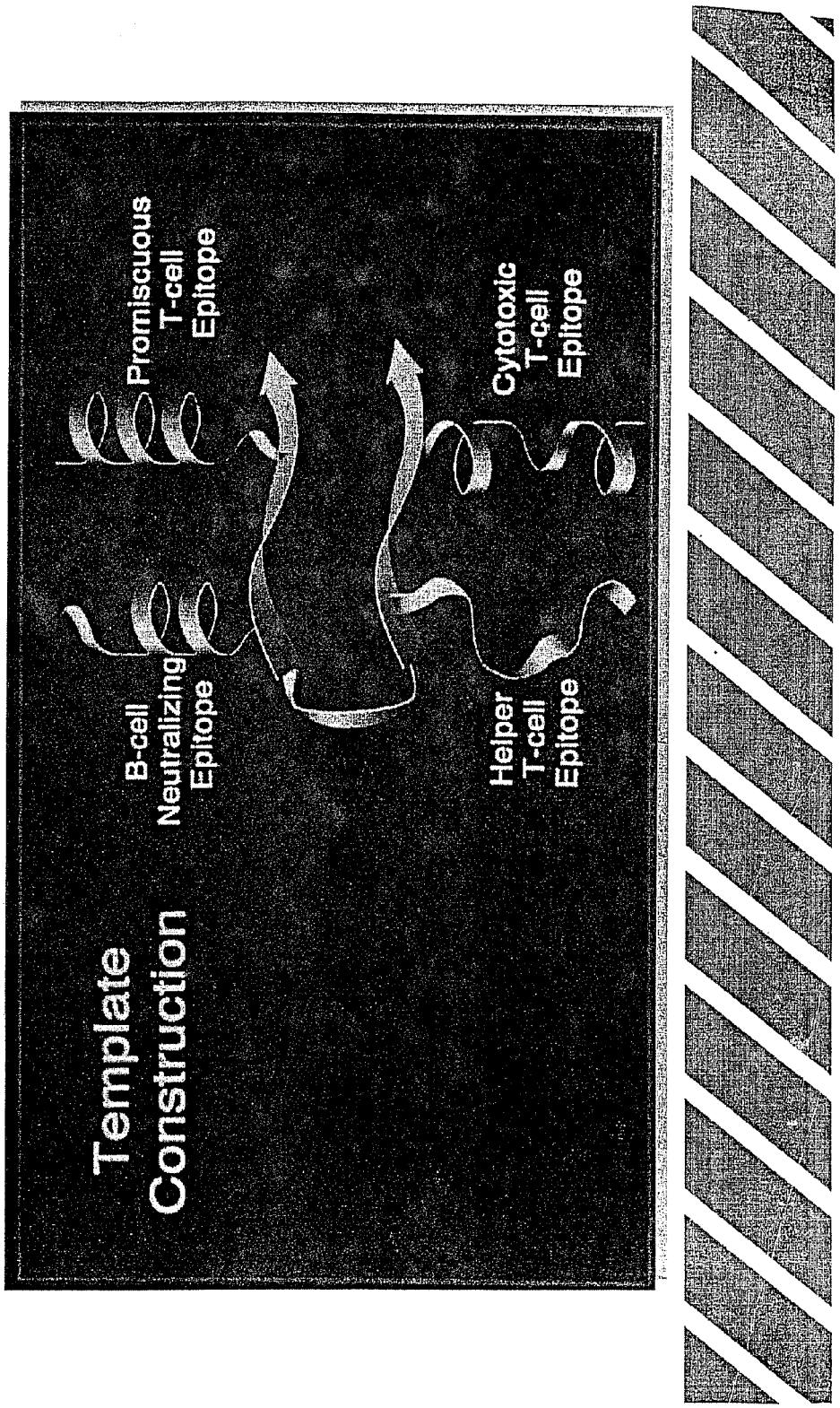
FIG. 2 is a schematic representation of a multivalent HER-2 B/CTL peptide.

The present invention provides peptides that are immunogenic epitopes of the HER-2 protein, referred to hereinafter as HER-2 B cell epitopes and HER-2 CTL epitopes.

The HER-2 B cell epitopes are capable of invoking a humoral response which results in the production of antibodies that are immunoreactive with the extracellular domain of the HER-2 protein. HER-2 protein, and its rat homolog neu, are transmembrane proteins with a relative molecular mass of 185 kd that is approximately 1255 amino acids (aa) in length. HER-2/neu protein has an extracellular binding domain (ECD) of approximately 645 aa, with 40% homology to epidermal growth factor receptor (EGFR), a highly hydrophobic transmembrane anchor domain (TMD), and a carboxyterminal cytoplasmic domain (CD) of approximately 580 aa with n 80% homology to EGFR. The amino acid sequence of the HER-2 protein and a nucleotide sequence which encodes such amino acid sequence are shown in GenBank Accession No. M11730.

The HER-2 B cell epitopes encompass peptides having one of the sequences, referred to hereinafter as the "reference sequences", shown in Table I below. The reference sequences were selected and scored using computer-aided analysis using six correlates of antigenicity: (a) the profiles of chain flexibility and mobility of individual sequences was calculated according to Karplus and Schultz, Naturwiss 72:212-213, 1985; (b) hydropathy profiles were generated over a seven residue span setting and were finally smoothed with a three residue span using the scale of Kyte and Doolittle, J. Moi. Biol. 157:105-132, 1982; (c) hydrophilicity profiles were generated over a 6-residue window using the program of Hopp and Woods, Proc. Natl. Acad. Sci. USA 78:3824-3828, 1981; (d) analysis of the exposure of an amino acid residue to water using a 1.4 Å probe) was carried out b the solvent exposure algorithm of Rose, Science 229:834-838, 1985; (e) protrusion indices that predicts portions of proteins that are accessible and protrude into the solvent were calculated by the method of Thornton, EMBO J. 5:409-413, 1986; (f) the probability that a five residue sequence is antigenic was determined by the method of Welling, FEBS Lett 188:215-218, 1985. The basic premise is that the algorithms used in the predictions will always locate regions that are surface-exposed on the protein and therefore most likely to be involved in antibody binding. Sequences were given a score of 1 to 6 based on their respective index values and were ranked: the highest ranking sequences had the highest individual score for the analyses examined (6/6), and successive candidates had the next highest score (5/6), etc. The best scoring epitopes were further ranked by correlation with their secondary structural attributes, e.g.., an amphiphilic α-helical sequence or a β-turn loop region are preferred over a random coil fragment. Computer programs by Chou and Fasman, Adv. Enzymol. Relat. Subj. Biochem. 47: 45-148, 1978 were used to predict the secondary structure (α-helix, β-strand/sheet, (3-turn/loop, random coil) and helical amphiphilic moment. Electrostatic ion pairs and helix dipole interaction in helical segment were also considered (e.g., hydrophobic/hydrophilic balance). Preferably, the hydrophilic/hydrophobic balance is from 2/2 to 4/1.

As described herein, the HER-2 B cell epitopes also encompass peptides that are functional equivalents of the peptides shown in Table I below. Such functional equivalents have an altered sequence in which one or more of the amino acids in the corresponding reference sequence is substituted or in which one or more amino acids are deleted from or added to the corresponding reference sequence. For example, cysteine residues may be deleted or replaced with other amino acids to prevent formation of incorrect intramolecular disulfide bridges upon renaturation. Optionally, the HER-2 B cell epitopes are glycosylated.

While it is possible to have nonconservative amino acid substitutions, it is preferred that, except for the substitutions that are made to replace cysteine, the substitutions be conservative amino acid substitutions, in which the substituted amino acid has similar structural or chemical properties with the corresponding amino acid in the reference sequence. By way of example, conservative amino acid substitutions involve substitution of one aliphatic or hydrophobic amino acids, e.g., alanine, valine, leucine and isoleucine, with another; substitution of one hydroxyl-containing amino acid, e.g., serine and threonine, with another; substitution of one acidic residue, e.g., glutamic acid or aspartic acid, with another; replacement of one amide-containing residue, e.g., asparagine and glutamine, with another; replacement of one aromatic residue, e.g., phenylalanine and tyrosine, with another; replacement of one basic residue, e.g., lysine, arginine and histidine, with another; and replacement of one small amino acid, e.g., alanine, serine, threonine, methionine, and glycine, with another.

Preferably, the deletions and additions are located at the amino terminus, the carboxy terminus, or both, of one of the sequences shown above. As a result of the alterations, the HER-2 B cell epitope equivalent has an amino acid sequence which is at least 70% identical, preferably at least 80% identical, more preferably at least 90% identical, most preferably, at least 95% identical to the corresponding reference sequences. Sequences which are at least 90% identical have no more than 1 alteration, i.e., any combination of deletions, additions or substitutions, per 10 amino acids of the reference sequence. Percent identity is determined by comparing the amino acid sequence of the variant with the reference sequence using MEGALIGN project in the DNA STAR program.

For functional equivalents that are longer than a corresponding reference sequence, it is preferred that the functional equivalent have a sequence which is at least 90% identical to the reference sequence and the sequences which flank the reference sequence in the wild-type HER-2 protein.

TABLE 1

Consolidated Human p185 HER-2 predicted B cell epitopes listed in the order of ranking by amino acid residue numbers. Asparagine (N)-linked glycosylation sites are underlined in bold.

| Predictive Ranking | Residue | Amino Acid Sequence | Secondary Structure |
| --- | --- | --- | --- |
| 7 | 27-45 | Tgtdmklrlpaspethldm (SEQ ID NO:1) | 25-28 β 0 turn; 29-32 α helix; 35-38 β turn |
| 8 (DW5) | 115-136 | AVLDNGDPLNNTTPVTGASPGG (SEQ ID NO:2) | 116-135 β turn |
| 9 | 168-189 | LWKDIFHKNNQLALTLIDTNRS (SEQ ID NO:3) | 173-176 β turn; 177-181 α helix |
| 1 | 182-216 | TLIDTNRSRACHPCSPMCKGSRCWG ESSEDCQSLT (SEQ ID NO:4) | 184-212 β turn/loop |
| 6 | 270-290 | ALVTYNTDTFESMPNPEGRYT (SEQ ID NO:5) | 273-286 β turn; 278-280 α helix |
| 3 | 316-339 | PLHNQEVTAEDGTQR_A_EKCSKPCA (SEQ ID NO:6) | 319-324 α helix; 324-336 β turn. |
| 10 (DW1) | 376-395 | PESFDGDPASNTAPLQPE (SEQ ID NO:7) | 379-388 β turn |
| 12 (DW6) | 410-429 | LYISAWPDSLPDLSVFQNLQ (SEQ ID NO:8) | 413-421 β turn |
| 2 | 485-503 | LFRNPHQALLHTANRPEDE (SEQ ID NO:9) | 497-500 β turn; 499-504 α hehix |
| 11 | 560-593 | CLPCHPECQPQNGSVTCFGPEADQCVACAH YKDP (SEQ ID NO:10) | 561-572 & 589-593 β turn; 579-581 α helix |
| 4 | 605-622 | KPDLSYMPIWKFPDEEGA (SEQ ID NO:11) | 616-620 α helix |
| 5 (DW4) | 630-650 | ING_T_HSCVDLDDKGCPAEQRASP (SEQ ID NO:12) | 635-642 β turn; 643-646 α helix |

The present invention also provides chimeric peptides, referred to hereinafter as "chimeric HER-2 B cell peptides," which comprise HER-2 B cel epitope, a helper T (Th) cell epitope, preferably a promiscuous Th cell epitope, and a linker. Depending upon the promiscuous Th cell epitope used, the HER-2 B cell epitope is linked to either the amino or the carboxy terminus of the Th cell epitope. The location and selection of the Th cell epitope depends on the structural characteristics of the B cell epitope (whether alpha helical or beta-tun or strand, Methods for selecting suitable Th cell epitopes are described in Kaumaya et al., "DE NOVO" ENGINEERING OF PEPTIDE IMMUNOGENIC AND ANTIGENIC DETERMINANTS AS POTENTIAL VACCINES, in Peptides, Design, Synthesis and Biological Activity (1994), pp. 133-164, which is specifically incorporated herein by reference. A summary of the immune responses elicited a variety of promiscuous T-helper cell epitope containing B-cell epitope chimeras was presented in a review titled "Synthetic Peptides: Dream or Reality" by Kaumaya et al., and published in PEPTIDES IN IMMUNOLOGY, Wiley and Sons, Ltd. (1996).

The chimeric HER-2 B cell peptides are useful immunogens for inducing production of antibodies that interact with and bind to the extracellular domain of the HER-2 protein. The chimeric B peptides are also useful as laboratory tools for detecting antibodies to HER-2 protein in patient's sera. In accordance with the present invention it has been determined that the chimeric HER-2 B cell peptides MVF-HER-2 (628-647), HER-2 (376-395)-MVF, and HER-2 (410-429)-MVF invoked an antibody response in rabbits and that such antibodies (a) immunopreciptate HER-2 protein, (b) bind to intact HER 2 receptor on ER-2 overexpressing cells in culture, and (c) reduce proliferation of HER-2 overexpressing cells in vitro and in a xeonograft mouse model. It has also been determined that immunization of transgenic mice with the chimeric peptide MVF-HER-2 (628-647) retards tumnor development within such mice for at least 9 months post the time when control mice developed tumors.

The present invention provides HER-2 CTL epitopes which have the ability to invoke a cell-mediated responses to HER-2 protein. As used herein the term HER-2 CTL epitope encompasses peptides having one of the sequences shown below in Table 2 or a functional equivalent thereof. The functional equivalent has an amino acid sequence which is at least 80%, preferably at least 90% identical to one of the sequences, referred to as the "reference sequence," shown in Table 2 below. The ability of the functional equivalent to invoke a cell-mediated response to HER-2 protein or the extracellular binding domain of HER-2 protein is the same as or greater than the corresponding reference sequence.

TABLE 2

| HLA-A3: | 167-175 | (ILWKDIFHK (SEQ ID NO:21)); |
| --- | --- | --- |
| | 714-722 | (ILKETELRK (SEQ ID NO:22)); |
| | 754-762 | (VLRENTSPK (SEQ ID NO:23)) |
| HLA-B7: | 1159-1167 | (AARPAGATL (SEQ ID NO:24)); |
| | 35-43 | (LPASPETHL (SEQ ID NO:25)); |
| | 1101 | (LPTHDPSPL (SEQ ID NO:26)) |
| HLA-B27: | 7-15 | (CRWGLLLAL (SEQ ID NO:27)); |
| | 897-905 | (RRFTHQSDV (SEQ ID NO:28)); |
| | 433-441 | (GRILHNGAY (SEQ ID NO:29)) |
| H-2K$^d$: | 63-71 | a(TYLPTNASL (SEQ ID NO:30)); |
| | 553-561 | (EYVNARHCL (SEQ ID NO:31)); |
| | 440-448 | (AYSLTLQGL (SEQ ID NO:32)) |
| HLA-A2: | 5-13 | (ALCRWGLLL (SEQ ID NO:33)); |
| | 48-57 | (HLYQGCQV (SEQ ID NO:34)); |
| | 141-149 | (QLRSLTEIL (SEQ ID NO:35)); |
| | 435-443 | (ILHNGAYSL (SEQ ID NO:36)); |

TABLE 2-continued

| | |
| --- | --- |
| 661-669 | (ILLVVVLGV (SEQ ID NO:37)); |
| 789-797 | (DLTSTVQLV (SEQ ID NO:38)); |
| 851-859 | (VLVKSPNHV (SEQ ID NO:39)); |
| 369-378 | (KIFGSLAFL (SEQ ID NO:40)); |
| 654-663 | (IISAVVGIL (SEQ ID NO:41)) |

The present invention also provides chimeric peptides, referred to hereinafter as chimeric HER-2 CTL peptides which comprise one of the above described HER-2 CTL epitopes or a functional equivalent thereof. The chimeric HER-2 CTL peptides comprises three units. The first unit comprises a HER-2 CTL epitope or functional equivalent thereof. The second unit is a promiscuous T helper cell epitope. The second unit preferably is from about 14 to about 22, more preferably about 15 to 21, most preferably 16 amino acids in length. The third unit is a linker which joins the first and second units. The linker is an amino acid or, preferably, a peptide which is from about 2 to about 15 amino acids, more preferably from about 2 to about 10 amino acids, most preferably from about 5 to about 6 amino acids in length. The most preferred linker comprises the sequences: Gly-Pro-Ser-Leu, SEQ ID NO. 20.

The present invention also comprises a co-linear chimeric peptide which comprises multiple HER-2 CTL epitopes, which are linked to each other by a linker that is from 1-5 amino acids in length. Optionally, the linker comprises a proteolytic site. In one embodiment the linker comprises adjacent basic amino acid residues. Preferably, the co-linear chimeric peptide comprises a HER-2 CTL eptiope from class HLA-A3, a HER-2 CTL epitope from class HLA-B7, a HER-2 CTL epitope from class HLA-A2, and a HER-2 CTL epitope from class HLA-B27. The co-liner chimeric peptide further comprises a second unit which is a promiscuous Th epitope of from 14 to 22 amino acids in length. The second unit is linked to the amino terminus or the carboxy terminus of the first unit by the linker.

A. Preparation of Epitopes and Co-Linear Chimeric Peptides

The HER-2 B cell epitopes, CTL epitopes, chimeric, and multivalent peptides, preferably, are synthesized using commercially available peptide synthesizers. Preferably, the chemical methods described in Kaumaya et al., "DE NOVO" ENGINEERING OF PEPTIDE IMMUNOGENIC AND ANTIGENIC DETERMINANTS AS POTENTIAL VACCINES, in Peptides, Design, Synthesis and Biological Activity (1994), pp 133-164, which is specifically incorporated herein by reference, are used.

The HER-2 B cell epitopes, HER-2 CTL epitopes and chimeric peptides may also be produced using cell-free translation systems and RNA molecules derived from DNA constructs that encode the epitope or peptide. Alternatively, the epitopes or chimeric peptides are made by transfecting host cells with expression vectors that comprise a DNA sequence that encodes the respective epitope or chimeric peptide and then inducing expression of the polypeptide in the host cells. For recombinant production, recombinant constructs comprising one or more of the sequences which encode the epitope, chimeric peptide, or a variant thereof are introduced into host cells by conventional methods such as calcium phosphate transfection, DEAE-dextran mediated transfection, transvection, microinjection, cationic lipid-mediated transfection, electroporation, transduction, scrape lading, bollistic introduction or infection.

The HER2 B cell epitope, CTL epitope, and chimieric peptide may be expressed in suitable host cells, such as for example, mammalian cells, yeast, bacteria, insect cells or other cells under the control of appropriate promoters using conventional techniques. Suitable hosts include, but are not limited to, *E. coli, P. pastoris*, Cos cells and 293 HEK cells. Following transformation of the suitable host strain and growth of the host strain to an appropriate cell density, the cells are harvested by centrifugation, disrupted by physical or chemical means, and the resulting crude extract retained for further purification of the epitope or chimeric peptide.

Conventional procedures for isolating recombinant proteins from transformed host cells, such as isolation by initial extraction from cell pellets or from cell culture medium, followed by salting-out, and one or more chromatography steps, including aqueous ion exchange chromatography, size exclusion chromatography steps, and high performance liquid chromatography (HPLC), and affinity chromatography may be used to isolate the recombinant polypeptide. To produce glycosylated epitopes and chimeric peptides, it is preferred that recombinant techniques be used. To produce glycosylated epitopes and chimeric peptides which contain the same, it is preferred that mammalian cells such as, Cos-7 and Hep-G2 cells be employed in the recombinant tecdniques.

Naturally occurring variants of the HER-2 B epitopes and HER-2 CTL epitopes shown in tables 1 and 2 above may also be isolated by, for example, by screening an appropriate cDNA or genomic library with a DNA sequence encoding the polypeptide.

B. Preparation of Multivalent HER-2 B Cell Peptides, Multivalent CTL Peptides, and Multivalent B/CTL Peptides The preferred synthetic approaches for preparing the HER-2 multivalent peptides employ a combinatorial Fmoc/ tbutyl, Fmoc/benzyl and Boc benzyl strategy as well as a fourth level of differential protecting group (Npys) strategy. Details of such approach are presented in Larimore et al. (1995) Journal of Virology 69:6077-6089, which is specifically incorporated herein by reference.

C. Identifying Functional Equivalents of the HER-2 B Cell Epitopes Shown in Table 1

Functional equivalents of the HER-2 B cell epitopes shown above may generally be identified by modifying the sequence of the epitope and then assaying the resulting polypeptide for the ability to stimulate an immune response, e.g., production of antibodies. For example, such assays may generally be performed by preparing a chimeric peptide which comprises the modified polypeptide and a promiscuous Th cell epitope, injecting the chimeric peptide into a test animal and assaying for antibodies. Such antibodies may be found in a variety of body fluids including sera and ascites. Briefly, a body fluid sample is isolated from a warm-blooded animal, such as a human, for whom it is desired to determine whether antibodies specific for HER-2/neu polypeptide are present. The body fluid is incubated with HER-2/neu polypeptide under conditions and for a time sufficient to permit immunocomplexes to form between the polypeptide and antibodies specific for the protein and then assayed, preferably using an ELISA technique. In such technique, the colorimetric change is measured at 490 nm. Epitopes which induce production of antibodies that exhibit a titer equal to 10,000 or greater for HER-2/neu protein, are preferred. As used herein a titer of 10,000 refers to an absorbance value of 0.2 above background.

D. Methods of Identifying Functional Equivalents of the HER-2 CTL Epitopes Shown in Table 2

Functional equivalents of the HER-2 CTL epitopes shown above in Table 2 are identified by modifying the sequences and then assaying the resulting peptide for the ability to stimulate an immune response, e.g., activation of the Tc cell. In the first encounter with the CTL epitope, small numbers of immune T cells secrete lymphokines, proliferate and differentiate into effector and memory T cells. The primary immune response occurs in vivo but is difficult to detect in vitro. Subsequent encounter with the same HER-2 antigen (i.e., the CTL epitope) by the memory T cell leads to a faster and more intense immune response. The secondary response occurs either in vivo or in vitro. Accordingly, the in vitro response is easily gauged by measuring the degree of proliferation, the degree of cytokine production, or the generation of cytolytic activity of the T cell population re-exposed to the HER-2 antigen. Detection of the proliferation of T cells may be accomplished by a variety of Known techniques. For example, T cell proliferation can be detected by measuring the rate of DNA synthesis. T cells which have been stimulated to proliferate exhibit an increased rate of DNA synthesis. A typical way to measure the rate of DNA synthesis is, for example, by pulse-labeling cultures of T cells with tritiated thymidine, a nucleoside precursor which is incorporated into newly synthesized DNA. The amount of tritiated thymidine incorporated can be determined using a liquid scintillation spectrophotometer. Other ways to detect T cell proliferation include measuring increases in interleukin-2 (IL-2) production, $Ca.^{2+}$ flux, or dye uptake, such as 3-(4,5-dimethylthiazol-2yl)-2,5,-diphenyltetrazolium. Alternatively, synthesis of lymphokines (such as interferon-gamma) can be measured or the relative number of T cells that can respond to intact HER-2/neu protein may be quantified.

Polynucleotides

The present invention also provides isolated polynucleotides which encode the B cell epitopes, the CTL epitopes, and the chimeric peptides of the present invention. The present polynucleotides also encompass polynucleotides having sequences that are capable of hybridizing to the nucleotide sequences of under stringent conditions, preferably highly stringent conditions. Hybridization conditions are based on the melting temperature™ of the nucleic acid binding complex or probe, as described in Berger and Kimmel (1987) Guide to Molecular Cloning Techniques, Methods in Enzymology, vol 152, Academic Press. The term "stringent conditions, as used herein, is the "stringency" which occurs within a range from about Tm-5 (5° below the melting temperature of the probe) to about 20° C. below Tm. As used herein "highly stringent" conditions employ at least 0.2×SSC buffer and at least 65° C. As recognized in the art, stringency conditions can be attained by varying a number of factors such as the length and nature, i.e., DNA or RNA, of the probe; the length and nature of the target sequence, the concentration of the salts and other components, such as formamide, dextran sulfate, and polyethylene glycol, of the hybridization solution. All of these factors may be varied to generate conditions of stringency which are equivalent to the conditions listed above.

Polynucleotides comprising sequences encoding a HER-2 B cell epitope, a HER-2 CTL epitope or a chimeric peptide of the present invention may be synthesized in whole or in part using chemical methods or, preferably, recombinant methods which are known in the art. Polynucleotides which encode a HER-2 B cell epitope or a CTL epitope may be obtained by screening a genomic library or cDNA library with antibodies immunospecific for the HER-2 protein or the CTL protein, respectively, to identify clones containing such polynucleotide.

The polynucleotides are useful for producing a HER-2 B cell epitope, a CTL epitope or a chimeric peptide. For example, an RNA molecule encoding a multivalent chimeric peptide is used in a cell-free translation systems to prepare such polypeptide. Alternatively, a DNA molecule encoding a HER-2 B cell epitope, a CTL epitope or a chimeric peptide is introduced into an expression vector and used to transform cells. Suitable expression vectors include for example chromosomal, nonchromosomal and synthetic DNA sequences, e.g., derivatives of SV40, bacterial plasmids, phage DNAs; yeast plasmids, vectors derived from combinations of plasmids and phage DNAs, viral DNA such as vaccinia, adenovirus, fowl pox virus, pseudorabies, baculovirus, and retrovirus. The DNA sequence is introduced into the expression vector by conventional procedures.

Accordingly, the present invention also relates to recombinant constructs comprising one or more of the present polynucleotide sequences. Suitable constructs include, for example, vectors, such as a plasmid, phagemid, or viral vector, into which a sequence that encodes the HER-2 B cell epitiope, the HER-2 CTL epitope or the chimeric peptide has been inserted. In the expression vector, the DNA sequence which encodes the epitope or chimeric peptide is operatively linked to an expression control sequence, i.e., a promoter, which directs mRNA synthesis. Representative examples of such promoters, include the LTR or SV40 promoter, the *E. coli* lac or tip, the phage lambda PL promoter and other promoters known to control expression of genes in prokaryotic or eukaryotic cells or in viruses. The expression vector, preferably, also contains a ribosome binding site for translation initiation and a transcription terminator. Preferably, the recombinant expression vectors also include an origin of replication and a selectable marker, such as for example, the ampicillin resistance gene of *E. coli* to permit selection of transformed cells, i.e., cells that are expressing the heterologous DNA sequences. The polynucleotide sequence encoding the HER-B cell epitope, the HER-2 CTL epitope or the chimeric peptide is incorporated into the vector in frame with translation initiation and termination sequences. Preferably, the polynucleotide further encodes a signal sequence which is operatively linked to the amino terminus of the HER-2 B cell epitope, the HER-2 CTL epitope, or chimeric peptide.

The polynucleotides encoding the HER-2 B cell epitope, the HER-2 CTL epitope or the chimeric peptides comprising such epitopes are used to express recombinant peptide using techniques well known in the art. Such techniques are described in Sambrook, J. et al (1989) Molecular Cloning A Laboratory Manual, Cold Spring Harbor Press, Plainview, N.Y. and Ausubel, F. M. et al. (1989) Current Protocols in Molecular Biology, John Wile & Sons, New York, N.Y. Polynucleotides encoding the HER-2 B cell epitope, the HER-2 CTL epitope or the chimeric peptides comprising such epitopes are also used to immunize animals.

Pharmaceutical Compositions

Pharmaceutical compositions which comprise the chimeric and multivalent HER-2 B cell peptides, HER-2 CTL peptides, and the HER-2 B/CTL peptides or the polynucleotides which encode the same are preferably formulated for use as a pharmaceutical composition (e.g., an immunogenic composition or a vaccine). Such compositions generally comprise one or more of the HER-2 chimeric or multivalent peptides or the polynucleotides which encode the same in combination with a pharmaceutically acceptable carrier, excipient or diluent. Such carriers will be nontoxic to recipients at the dosages and concentrations employed.

In addition to the epitopes, multivalent peptides, and chimeric peptides (which functions as antigens) or the polynucleotide which encodes the same, other components, such as a vehicle for antigen delivery and immunostimulatory substances designed to enhance the protein's immunogenicity, are, preferably, included in the pharmaceutical composition. Examples of vehicles for antigen delivery include aluminum salts, water-in-oil emulsions, biodegradable oil vehicles, oil-in-water emulsions, biodegradable microcapsules, and liposomes. For the vaccines which comprise the chimeric peptide, the preferred vehicle for antigen delivery is a biodegradable microsphere, which preferably is comprised of poly (D, L-lactide-co-glycolide) (PLGA).

While any suitable carrier known to those of ordinary skill in the art may be employed in the pharmaceutical compositions of this invention, the type of carrier will vary depending on the mode of administration and whether a substantial release is desired. For parenteral administration, such as subcutaneous injection, the carrier preferably comprises water, saline, alcohol, a fat, a wax, or a buffer. Biodegradable microspheres (e.g., polylactic galactide) may also be employed as carriers for the pharmaceutical compositions of this invention. Optionally, the pharmaceutical composition comprises an adjuvant.

The HER-2 chimeric and multivalent peptides and the polynucleotides which encode the same are useful for enhancing or eliciting, in a subject or a cell line, a humoral response and, preferably, a cellular immune response (e.g., the generation of antigen-specific cytolytic T cells). As used herein, the term "subject" refers to any warm-blooded animal, preferably a human. A subject may be afflicted with cancer, such as breast cancer, or may be normal (i.e., free of detectable disease and infection). The pharmaceutical composition is particularly useful for treating women who have a family history of breast cancer or who have had breast tumors removed.

Methods of Treatment

The present invention also provides methods of treating a cancer which is associated with overexpression of the HER-2 protein. By "treating" is meant inhibiting or slowing or retarding the growth of the tumor . Such cancers include breast, lung, ovarian, bladder and prostate. The method comprises administering a pharmaceutical composition comprising one or more of the chimeric peptides or multivalent peptides of the present invention to a subject. Preferred multivalent peptides are those which comprise one or more of the following epitopes: HER-2 (628-647), HER-2 (316-339), and HER-2 (485-503). Preferably multiple intramuscular injections, at three week intervals are used to administer the pharmaceutical composition.

EXAMPLES

Exemplary methods are described below, although methods and materials similar or equivalent to those described herein can be used in the practice or testing of the present peptides, compositions and methods. All publications and other references mentioned herein are incorporated by reference in their entirety. The materials, methods, and examples are illustrative only and not intended to be limiting.

Peptide Synthesis and HPLC Purification. Peptides were synthesized as previously described (Kaumaya 1994). Briefly, peptides were synthesized on a Milligen/Biosearch 9600 peptide synthesizer, using a 4-methylbenzhydrylamine resin as the solid support (substitution 0.54 mm/g). The Fmoc/t-butyl synthetic method was employed using 4-(hydroxymethyl) phenoxyacetic acid as the linker. After the final deprotection step, protecting groups and peptide resin bond were cleaved with 90% TFA, 5% anisole, 3% thioanisole, 2% ethanedithiol. Crude peptide was purified by semipreparative HPLC using a Vydac C4 (10 mm×25 cm) column at 32.5° C. Buffers were 0.1% TFA in $H_2O$ and 0.1% TFA in acetonitrile. Peptides incorporate a "promiscuous" T cell epitopes MVF 288-302 (Kaumaya 1994): DW1MVF (HER-2 376-395), MVFDW4 (628-647), DW5MVF (115-136), DW6MVF (410-429).

Gel Filtration. 20 mg/ml acidified peptide solution (0.1 mg/ml in DTT) was loaded onto a Sephadex G-25 column and 5 ml fractions eluted with 0.1M HOAc. Peptide samples were measured spectrophotometrically at 235 nm and absorbance values plotted vs. time. Samples with absorbance values above 0.1 and eluting before DTT were pooled and lyophilized. The reaction was monitored for completion by Ellman's reagent at 410 nm.

Capillary Zone Electrophoresis. CZE was preformed on a Beckman P/ACE System 2100 interfaced with an IBM computer. Sample was voltage separated (15 kV) in 100 mM sodium borate using a 50 cm capillary over 20 min. Eluant was monitored at 214 nm.

Circular Dichroism and mass spectrometry. Measurements were preformed on a JASCO J-500 spectropolarimeter interfaced with an IBM computer. The instrument was calibrated in 0.06% (w/v) solution of ammonium-d-10-camphorsulfonate. The CD spectra of the peptides (62.5-250 uM by dilution of peptide stocks in water) were measured at ambient temperature in a 0.1cm path length cylindrical quartz cuvette (Hellma). Mean residue ellipticity (mdeg) was calculated using the relationship $[\theta]=100 \theta/cnl$ where is the ellipticity, c is the peptide concentration (mM), n is the number of amino acids in the peptide, and 1 is the path length (cm).

Fast atom bombardment (FAB) mass spectrometry measurements were carried out on a inneganMat-900 instrument.

Mercuric Acetate. Peptide was dissolved in a minimal amount of water and 100 mg/mm S-tBu solution (2-10 fold excess) added. Peptide was placed under vacuum and precipitated by 2-Mercaptoethanol in a 55° C. water bath under stirring. After filtering through dampened Celite, the filtrate was rotary evaporated, acidified with 0.1% TFA in water and lyophilized.

Biological Procedures

Immunizations and animals. Female New Zealand white rabbits were obtained from Mohican Valley Rabbitry (Loudenville, Ohio). Rabbits were immunized subcutaneously at multiple sites with a total of 1mg of peptide emulsified in CFA. Subsequent booster injections (1 mg and 500 µg in PBS) were given three and six weeks after the primary immunization. Sera were collected and complement inactivated by heating to 56° C. for 30 min. Sera aliquots were stored at −5 to −15° C. Antibodies were purified by ammonium sulfate precipitation: A stock solution of saturated ammonium sulfate solution (SAS) was prepared, autoclaved and cooled to 4° C. Antibody was allowed to precipitate by slowly adding SAS to 35% v/v under stirring in cold room. Samples were centrifuged 14,000 ×g 20 min and the supernate stored at −20° C. The pellet was dissolved with 0.1M PBS in ½ original volume. Fractions were then placed in Slide-a-lyzer cassettes (Pierce) and dialyzed against frequent changes of >200 volumes pH 8, 0.15M NaCl. The saline was brought to pH 8 with a few drops of 0.1M NaOH. IgG concentration was determined by radial immunodiffusion (RID) (The Binding Site, UK ). Monoclonal antibodies were purchased from Oncogene Science.

Direct ELISA. IJ-bottom polyvinyl chloride plastic assay plates were coated with 100 µl of antigen at 2 µg/ml in PBS overnight at 4° C. Nonspecific binding sites were blocked for 1 hour with 200 µl PBS-1% BSA and plates were washed with PBT (phosphate-buffered saline containing 0.05% Tween 20 and 1% horse serum). Rabbit antiserum 1/500 or mouse antiserum 1/50 in PBT was added to antigen coated plates, serially diluted 1:2 in PBT, and incubated 2 hr at room temperature. After washing the plates, 50 µl of 1/500 goat anti-rabbit or goat anti-mouse IgG conjugated to horseradish peroxidase (Pierce Chemical Co.) was added to each well. Excess antibody conjugate was removed, and bound antibody was detected using 50 µl of 0.15% $H_2O_2$ in 24 mM citric acid, 5 mM sodium phosphate buffer, pH 5.2, with 0.5 mg/ml 2,2'-aminobis(3-ethylbenzthiazoline-6-sulfonic acid) as the chromophore. Color development was allowed to proceed for 10 min and the reaction was stopped with 25 µl of 1% sodium dodecylsulfate. Absorbance was determined at 410 nm using a Dynatech MR700 ELISA reader. Results are expressed as the mean absorbance of duplicate wells after subtraction of background.

Cell Culture. Stock cultures were maintained at 37° C. in a 5% $CO_2$ incubator. All cell culture media, FCS, and supplements were purchased from GEBCO (Grand Island, N.Y.). The human breast adenocarcinoma cell lines SKBR-3 and MCF-7 were obtained from the American Type Culture Collection and was subcultured in McCoy's 5A or DMEM supplemented with 10% FCS and L-glutamine. Cav-1 was maintained in RPMI 1640 with 10% FCS and L-glutamine. Cav-was derived from a fresh colon tumor specimen which was cryopreserved and subsequently cultured; it does not express detectable levels of HER-2/neu. SKBR3 is a breast tumor cell line which overexpresses the HER-2 protein while MCF-7 expresses the normal concentration of protein.

Immunoprecipitation and Western Blotting. On day zero, $1.0\times10^7$ SKBR3 cells were plated in 75 $cm^3$ cell culture flasks and allowed to adhere overnight. Anti-peptide antibodies were added (100 µg/ml) for 4 hrs. The reaction was stopped by aspirating the media and immediately adding ice cold 0.1M phosphate buffered saline (PBS). Cells were trypsinized and washed twice with cold Hank's Balanced Salts Solution (HBSS). Cold lysis buffer (150 mM NaCl; 50 mM Tris, pH 8; 10 mM EDTA, 10 mM sodium pyrophosphate, 10 mM sodium fluoride; 1% NP-40, 0.1% SDS) containing 3 mM $Na_3VO_4$, 10 µg/ml each aprotinin and leupeptin was added to cells resuspended in 100 µl HBSS. Lysis was achieved by gentle rotation at 4° C. for 20 min. After centrifugation (14,000×g, 20 min) to remove cell debris, lysates were incubated with 3-5 µg antibody and 30 µl Protein A/Protein G (Oncogene Science) overnight. Beads were pelleted by centrifugation (14,000×g 30 sec), washed twice in lysis buffer containing 1 mM $Na_3VO_4$ and boiled in SDS sample buffer 5 min.

Proteins were resolved by 7.5% SDS-PAGE, transferred to nitrocellulose and probed with antibody. Protein transfer was monitored with prestained molecular mass standards (Bio-Rad). Immunoreactive bands were detected using horse radish peroxidase conjugated goat anti rabbit immunoglobins by enhanced chemiluminescence (Amiersham).

Indirect Binding Assay. SKBR3 cells or MCF-7 cells were plated at 5,000 cells/well in V-bottom plates (Linbro, McLean Va.). The cells were incubated with various concentrations of antibodies. After being washed with Hank's Balanced Salts Solution (HBSS) the cells were incubated for one hour with fluorescein isothiocyanate (FITC)-conjugated goat anti-rabbit or goat anti-mouse antibody and fixed with formalin. A mouse monoclonal Ab (Oncogene Science, Cambridge, MA) was used as the positive control and an anti-CD3 Ab as the negative control. The cells were analyzed by a Coulter ELITE flow cytometer (Coulter, Hialeah, Fla.), which has an argon laser for excitation at 488 mn, and a 525 run band pass filter for FITC fluorescence 5.0×10³ cells were counted for each sample and final processing was performed. Debris, cell clusters and dead cells were gated out by light scatted assessment before single parameter histograms were drawn.

Effect of Abs on cell proliferation. SKBR3, MCF7 and CAVI cells were plated 5,000 cells/well in V-bottom plates along with various concentrations of Ab on day zero. On day 3, cells were pulsed with [3H] thymidine (1 μCi/well) at which time they were placed in a 20° C. freezer for 1 h. After thawing at room temperature cells were harvested an a PHD cell harvester (Cambridge Tech, Inc.). Samples were incubated in 5 ml Ready Safe liquid scintillation cocktail (Beckman) and radioactivity determined by beta counter. Results are expressed as the mean CPM +/− the standard deviation (SD).

CTL Assay: In vitro stimulation. Inguinal and periaortic lymph nodes (LN) are removed 7-10 days after immunization. LN cells (4×10⁶ 5×10⁶) are then stimulated in vitro by coculturing with 1.5×10⁵ irradiated (10 000 rad) P815 cells prepulsed for 1h with 1 μM of the appropriate CTL peptide. The culture medium used is cDMEM (DMEM supplemented with 10% FCS). Supernatant containing 30 U/ml (final) of IL-2, 2 mM L-glutamine, 10 mM Hepes and 5×10⁵ M-2-mercaptoethaniol).

Seven days after in vitro stimulation, the CTL activity is tested in a standard chromium-release assay. P815 cells (10⁶) are labeled with 150 μCi sodium [$^{51}$Cr] chromate for 1 h at 37° C. in the presence or absence of the appropriate peptide (1 μM) and washed three times. Labeled targets (2×10³) are co-incubated with stimulated LN cells at predetermined ratios in 200 μl volumes in V-bottom 96 well plates. After a 4 h incubation at 37° C., the supernatants (100 μl) are harvested for γ-counting. The % specific lysis is calculated as 100×[(experimental−spontaneous release)/(total−spontaneous release)] (Valmori, et al. 1994).

Effect of antibodies in vivo. HER2 cells (3×10⁶) were suspended in 250 μl PBS, mixed with 250 μl MATRIGEL (Beckton Dickinson) on ice and injected subcutaneously into mice. Polyclonal antibodies to a total concentration of 2 mg/mouse, were injected i.p. on days 9 and 11. Tumor volume was measured twice weekly with calipers and calculated by the formula (length×width×height).

Example 1

Peptide DWI MVF; HER-2 (376-395) MVF

The epitope, named DWI, comprises amino acids 376-291 of the HER-2 protein linked to the promiscuous Th cell epitope MVF. DW1 is predicted to be (X-helical with a slight turn propensity.

Synthesis. The 20 amino acid HER-2 sequence was attached to the N-terminus of MVF 288-302 by the four amino acid linked sequence Gly-Pro-Ser-Leu SEQ ID NO. 20. The resulting peptide was named DW1MVF indicating DW1 placement at the N-terminus as opposed to MVFDW1 which would represent C-terminal position. The first amino acid was joined manually and completion monitored by Kaiser ninhydrin test. Subsequent couplings were performed on the Milligen/Biosearch 9600 peptide synthesizer. After final deblocking the peptide was cleaved from the resin with Reagent PU. An extended cleavage time is necessary since the peptide contains Arg -2,2,5,7,8-pentamethylchroman-6-sulfonyl(PMC) and His. (A yellow cleavage solution is observed when histidine is present).

Purification and characterization. The peptide was rotary evaporated to remove TFA, precipitated with cold ether, and water/ether extracted. Extraction was fairly easy and HPLC analysis of the gel filtered lyophilized peptide showed few deletion peptides. The peptide eluted as 2 peaks prior to DTT. These were pooled and subjected to analytical HPLC.

Analytical BPLC of semiprep purified DW1MVF identified one major peak while CZE identified three species of differential charge. The complete peptide contains 6 negative and 4 positively charged species at neutral pH. Mass spectrometry results confirmed the major peak as the epitopes of interest with a molecular weight of 4472. The CD spectra of peptides in dilute aqueous acetic acid indicate slight random coil. In TFE, the conformation shifts to a slight α-helix with a strong maximum in the 190-195 nm range and minima at 208 and 222 nm. Helicity of peptide [θ$_{222}$, −5,000] was calculated using Chen's equation with reference to the mean ellipticity of polylysine for 100% helix θ$_{222}$=−33,000.

Example 2

Peptide MVFDW4; HER-2 (628-647) MVF

MVFDW4 comprises an altered sequence of the peptide extending from amino acid 628 through 647 Of the HER-2 protein. The native sequence contains 3 cysteine residues whose disulfide bonding pairs are unknown. Since the cysteines at position 634 and 642 had the potential to form a bridge, Cys 630 was substituted with Gly. Substituting glycine for cysteine is one way to preserve the relative size of the R group at that position. Synthesis proceeded by first making the DW4 (628-647) peptide attached to the linker then extending the sequence N-terminally by addition of the NWF (288-302) T helper cell sequence. This produced the MVFDW4 peptide.

In order to create the disulfide bond, the tBut protecting group was cleaved giving the free thiol form. The mercuric acetate/2-mercaptoethanol procedure reduces production of disulfide bonded multimers. Analytical HPLCs of the crude product and samples were compared. In the crude sample, two sharp peaks are immediately followed by a broad ill-defined shoulder. The treated sample showed a reduction in the size of the leading peak and a broader second peak. The correct fraction was later identified by mass spectrometry which confirmed the molecular weight of the peptide as 4612.

To deduce the identity of the new peaks hydrogen peroxide or dithiothreitol (DTT) was added to the crude samples. Addition of hydrogen peroxide causes oxidation.

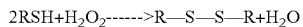

This reaction produced a single major peak that eluted at 11.5 minutes. This corresponds with the leading peak of the crude sample. DTT treatment causes reduction by the following reaction scheme:

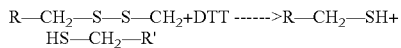

The profile of the DTT treated product resembled the starting material. These profiles reveal that the starting material is a mixture of reduced and oxidized peptide. Mercuric acetate treatment shifts the concentration in favor of the reduced species.

Example 3

Peptide DW5MVF; HER-2 (115-136) MVF

Synthesis: MVF 288-302 plus the four residue amino acid linker was connected to the resin as described above in example 1 and the sequence continued with amino acids 115-136 of the HER-2 protein. This produced the peptide DW5MVF. The sequence is predicted to be β-turn with high aggregation potential. This necessitated double coupling critical residues A115, V116, T127, V129 and S133.

Purification and characterization: DW5MVF was cleaved and extracted with ether and water. Extraction was quite difficult as the peptide formed dense, sticky aggregates which were only minimally soluble by addition of acetic acid. Analytical HPLC of the crude sample showed one predominant peak with a minor doublet. Semipreparative HPLC was used to separate the doublet. The lyophilized sample was readily dissolved in dilute acetic acid for analytical HPLC. A sample was subjected to time of flight mass spectrometry and yielded a molecule of the correct molecular weight 4431. The peptide elutes as a single peak at 15.5 min.

Example 4

Peptide DW6MVF; HER-2 (410-429) MVF

Residues 410-429 of HER-2, named DW6, represents a potential immunogenic epitopes from the same region as DW1MVF. Due to the success of DW1MVF in early FACS experiments we wished to raise additional antibodies to this region. Residues 410-429 were synthesized as previously described by N-terminal addition to the MVF/4-residue-linker sequence. The final product was DW6MVF. It is predicted to be a β-turn with moderate to high aggregation potential at its C-terminus.

Synthesis. The DW6 sequence was attached to the C-terminal resin linked MVF sequence using FMOC chemistry. Computer algorithms predicted high aggregation potential therefore extended coupling times and/or double coupling was used to try to minimize aggregation.

Purification and characterization: TFA cleavage yielded DW6MVF peptide which was ether/water extracted. This workup as well proved to be difficult due to the high degree of aggregation. There was a significant concentration of deletion peptides as shown by HPLC. Semipreparative BPLC separated the major peak which eluted at 13-14.5 minutes. Analytical BPLC showed a single peak that eluted at 17 min. The difference in retention time for semipreparative HPLC and analytical HPLC is due to a 3 minute difference in the time of sample injection. Amino acid analysis confirmed its identity as the peptide of interest. Derivatized amino acids were analyzed as their phenylthiohydanton derivatives, (observed (theory): Asp (2.99 (3)), Glu (4.32 (4)), Ser (4.77 (5)), Gly (3.53 (4)), His (1.62(2)), Arg (1.08)), Thr (0.02(0)), Ala (0.97 (1)), Pro (3.02 (3)), Tyr (0.95 (1)), Val (3.86 (4)), Met (0.09 (0), Cys (0)(0)), Ile (2.87(3)), Leu (9.34(9)), Phe (0.93 (1)), Lys (2.28(2)) and Tip (0(0)).

Examples 5 and 6

DW2 (391-399) and DW3 (376-399)

DW2 comprises amino acids 391-399 of the HER-2 protein. DW3 comprises amino acids 376-399 of the HER-2 protien.

Synthesis: Residues 391-394 were attached to the resin. Synthesis was continued using the remainder by addition of residues 376-390. This gave a final peptide (DW3) of 376-399.

Purification and characterization: Semipreparative HPLC separated the major peak (eluting at 11 minutes) of a triplet from DW2. DW3 gave two major peaks of mixed composition. Mass spectrometry determined that the fi-action eluting at 11 minutes in DW2 was the correct peptide with a molecular mass of 1052. No further characterization was done on DW3.

Immunogenicity of the Chimeric Peptides of Examples 1-6

Chimeric peptides prepared as described above in example 1-6 are highly immunogenic as evidenced by high antibody titers as early as the third week post immunization. Sera obtained weekly was assayed for their ability to recognize and bind to the peptide sequence. DW5MVF showed a steady rise in antibody titers. Titers for DW5MVF were higher in one rabbit than the other. Rabbit 1 showed an immediate, vigorous response to peptide immunogen while Rabbit 2 gave a slow but steady rise in antibody titer. MVFDW4 produced the most immediate and vigorous response. These exceptionally high titers remained at maximal levels through four weeks after the tertiary boost. Peptide DW6MVF gave the lowest titers of the four antibodies but responses were stable and comparable between rabbits. The polyclonal IgG sera did not cross react with the MVF T-cell sequence. All results were obtained in an outbred population indicating the broad immunogenicity of the peptides in rabbits.

Specificity of Peptide Antibodies for HER-2

Figure 3:
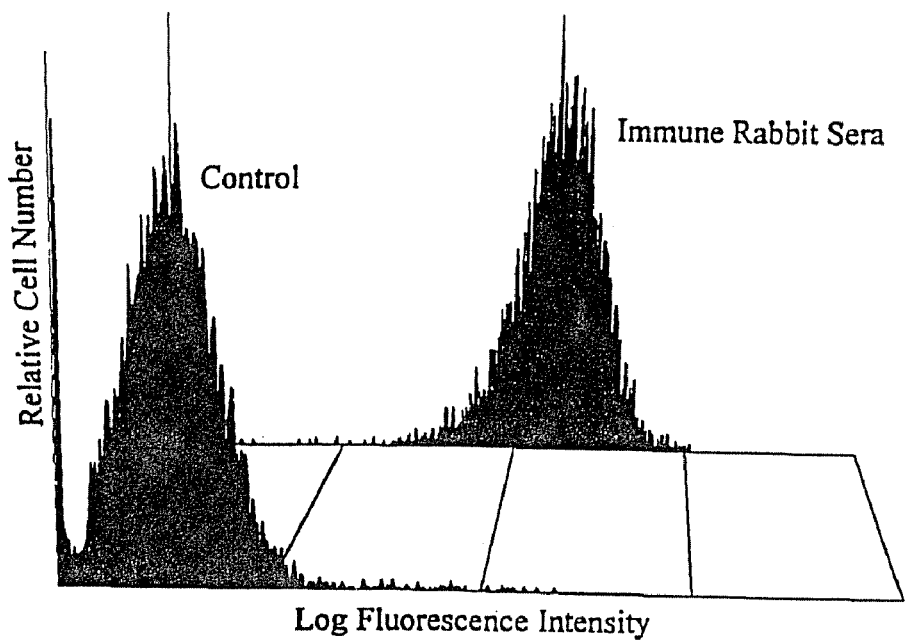
FIG. 3 shows the binding of antibodies raised to the chimeric HER-2 B cell peptide DW1MVF to HER-2 overexpressing SKB3 cells. Antibodies raised to DW1MVF specifically bound the HER-2 receptor with an affinity comparable to a commercially available monoclonal antibody. SKBR3 cells were incubated with antibody, washed and FITC-conjugated secondary antibody added. After being fixed in formalin, cells were analyzed by a Coulter ELITE flow cytometer at 488 nm for excitation. $5.0 \times 10^{6^6}$ cells were counted for each sample.
Figure 3:
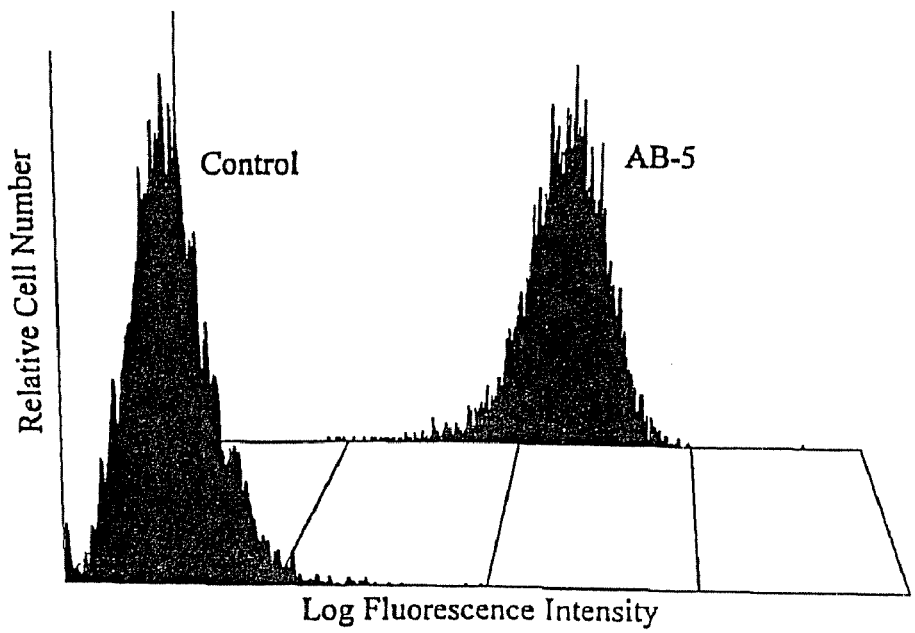
Figure 4:
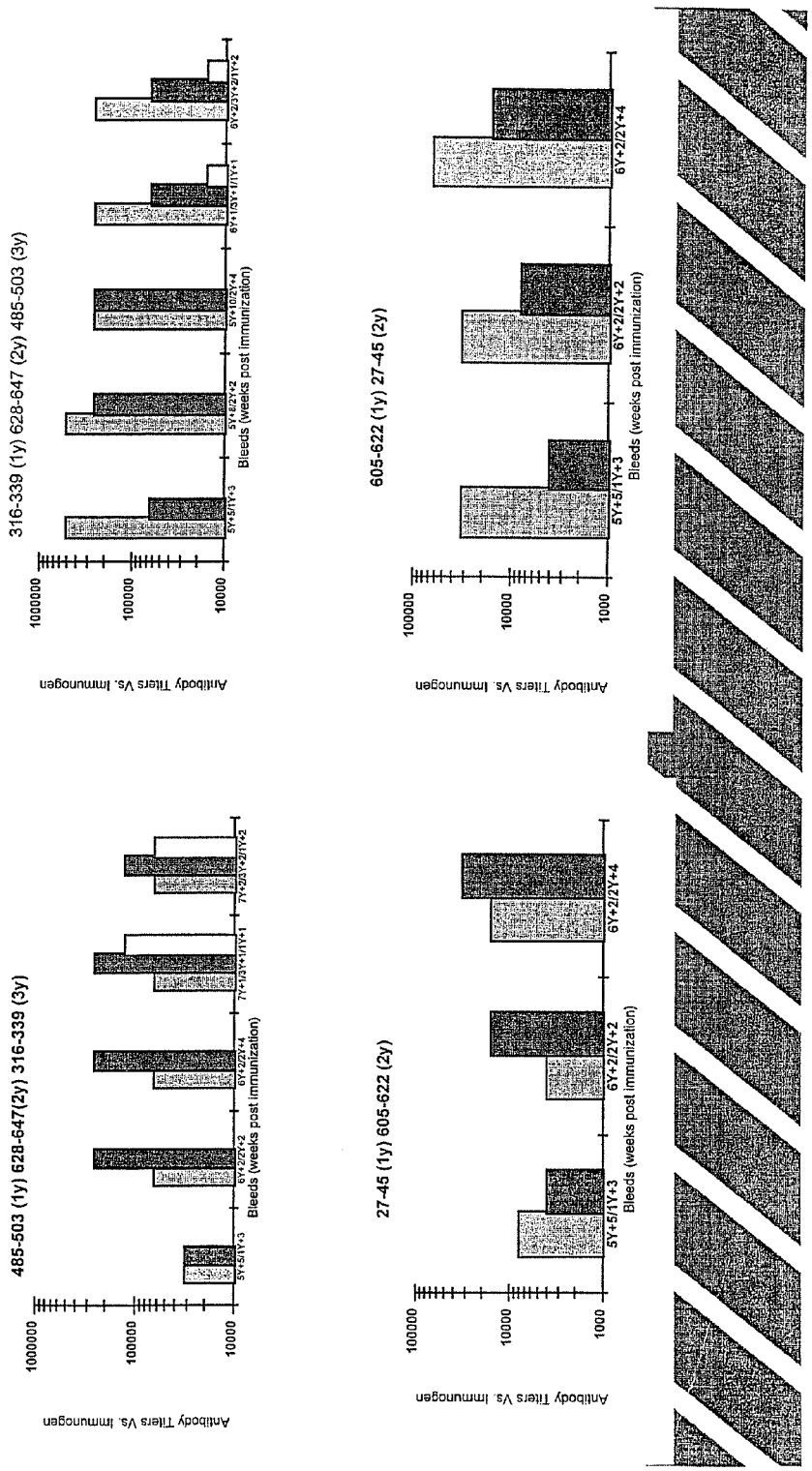
FIG. 4 shows the immunogenicity in outbred rabbits injected with multiple chimeric HER-2 B cell peptides.
Figure 5:
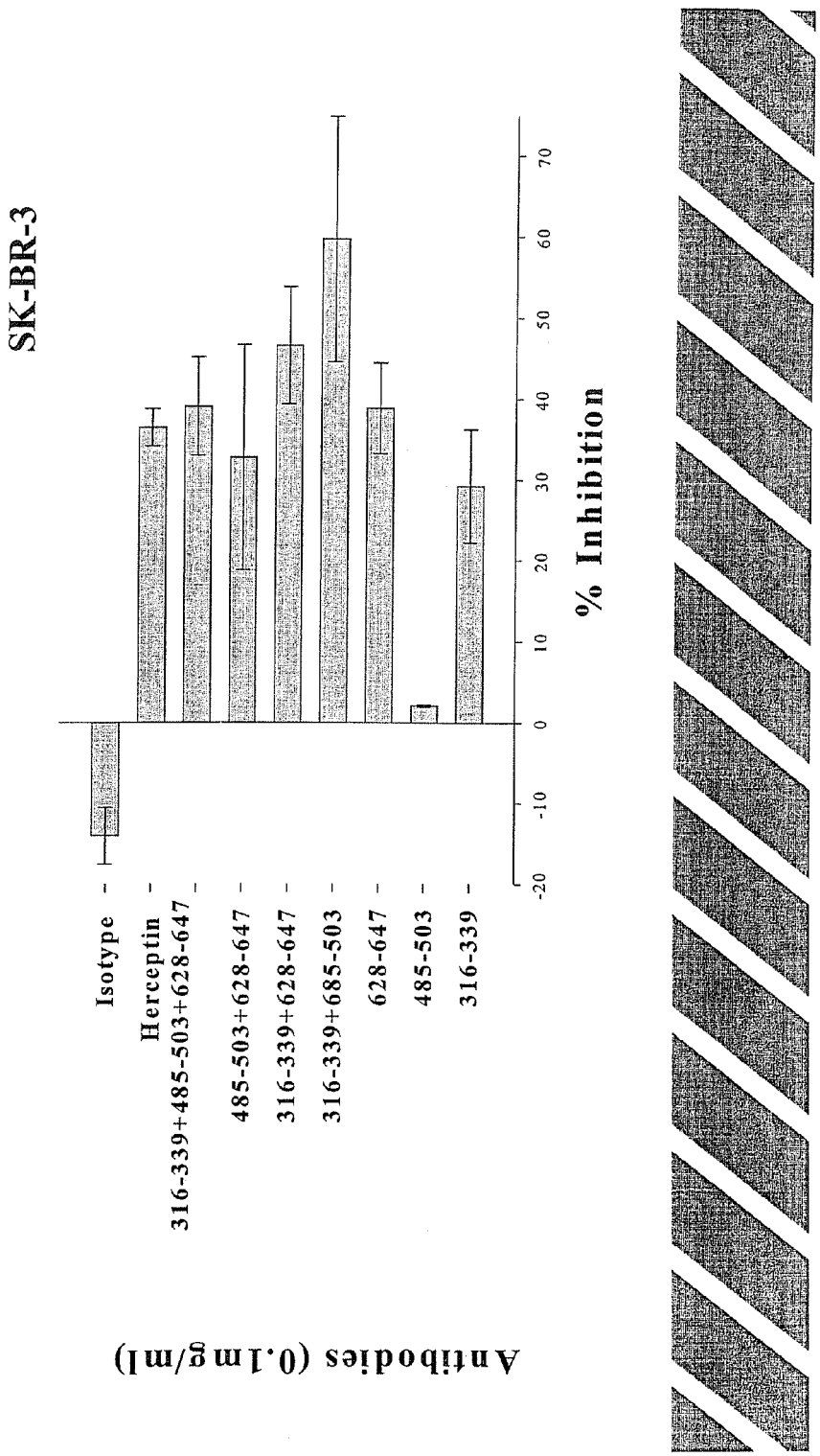
FIG. 5 shows the antiproliferative effects of peptide antibodies generated against herceptiin and single and multiple HER-2 B cell chimeric peptides MVFDN1 (HER-2 (27-45)), MVFDN2 (HER-2 (316-337)), MVFDN3 (HER-2 (485-503) and MVFDW4 (DW4) on HER-2 overexpressing SK-BR-3 human breast cancer cells. Results are average of triplicate samples FIG. 6 shows the antiproliferative effects of peptide antibodies generated against herceptin HER-2 B cell chimeric peptides MVFDN1 (ND1) MVFDN2 (N2), MVFDN3 (N3) and MVFDW4 (DW4) on HER-2 overexpressing BT474 human breast cancer cells. Results are average of triplicate samples.
Figure 6:
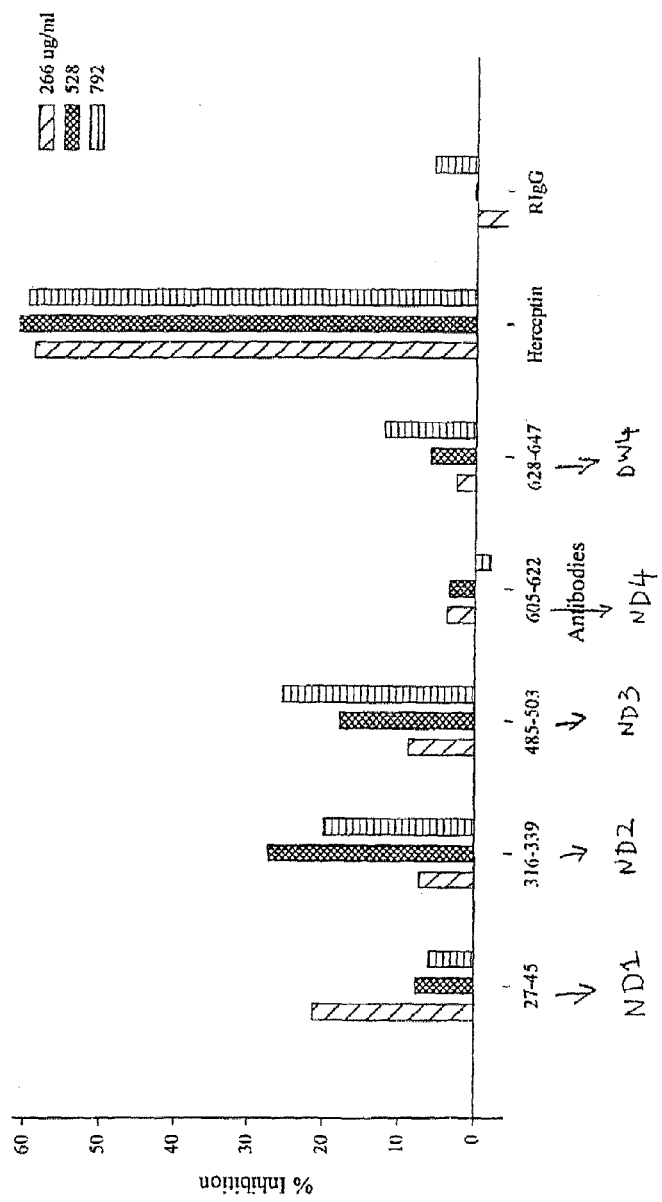
Figure 7:
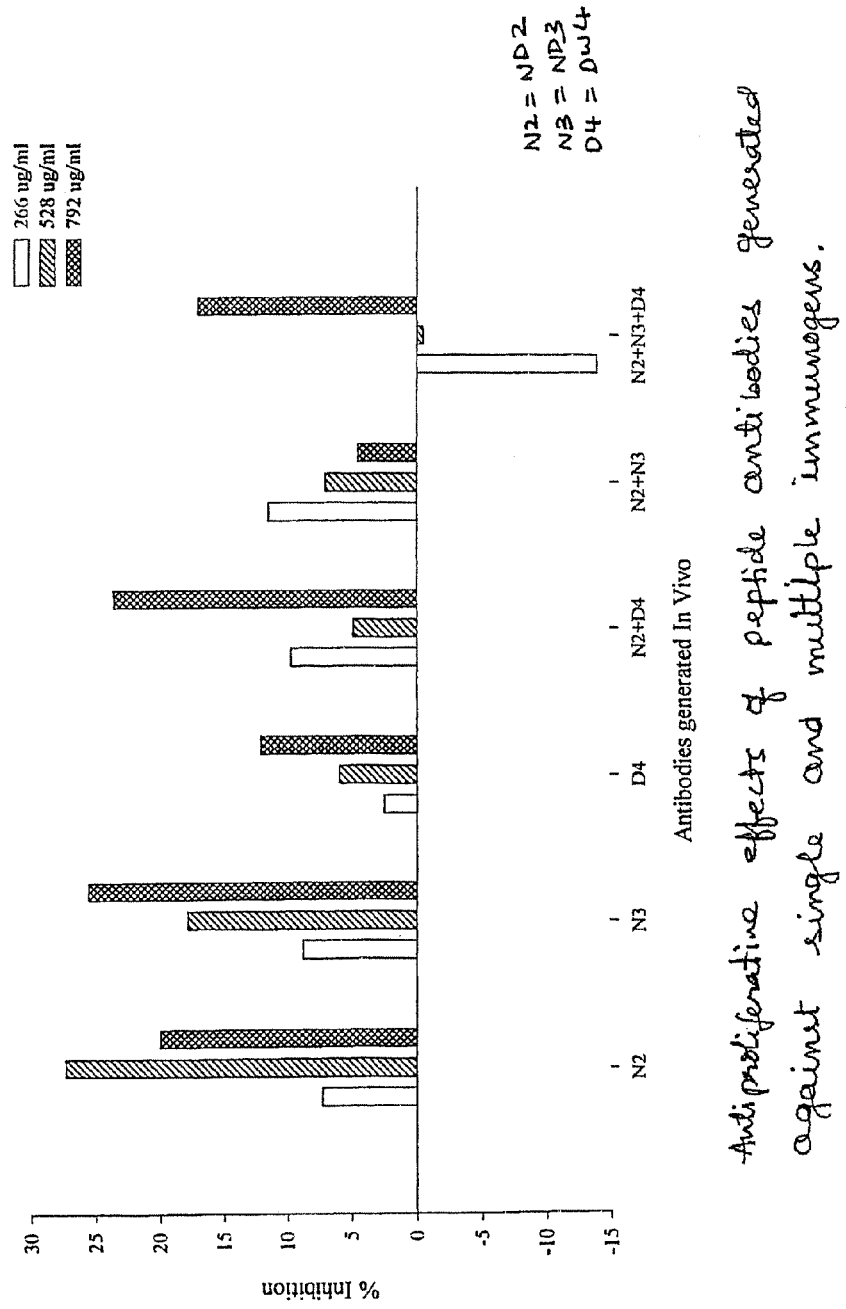
FIG. 7 shows the antiproliferative effects of peptide antibodies generated against single and multiple HER-2 B cell chimeric peptides MVFDN2 (N2), MVFDN3 (N3) and MVFDW4 (DW4) on HER-2 overexpressing BT474 human breast cancer cells. Results are average of triplicate samples.
Figure 8:
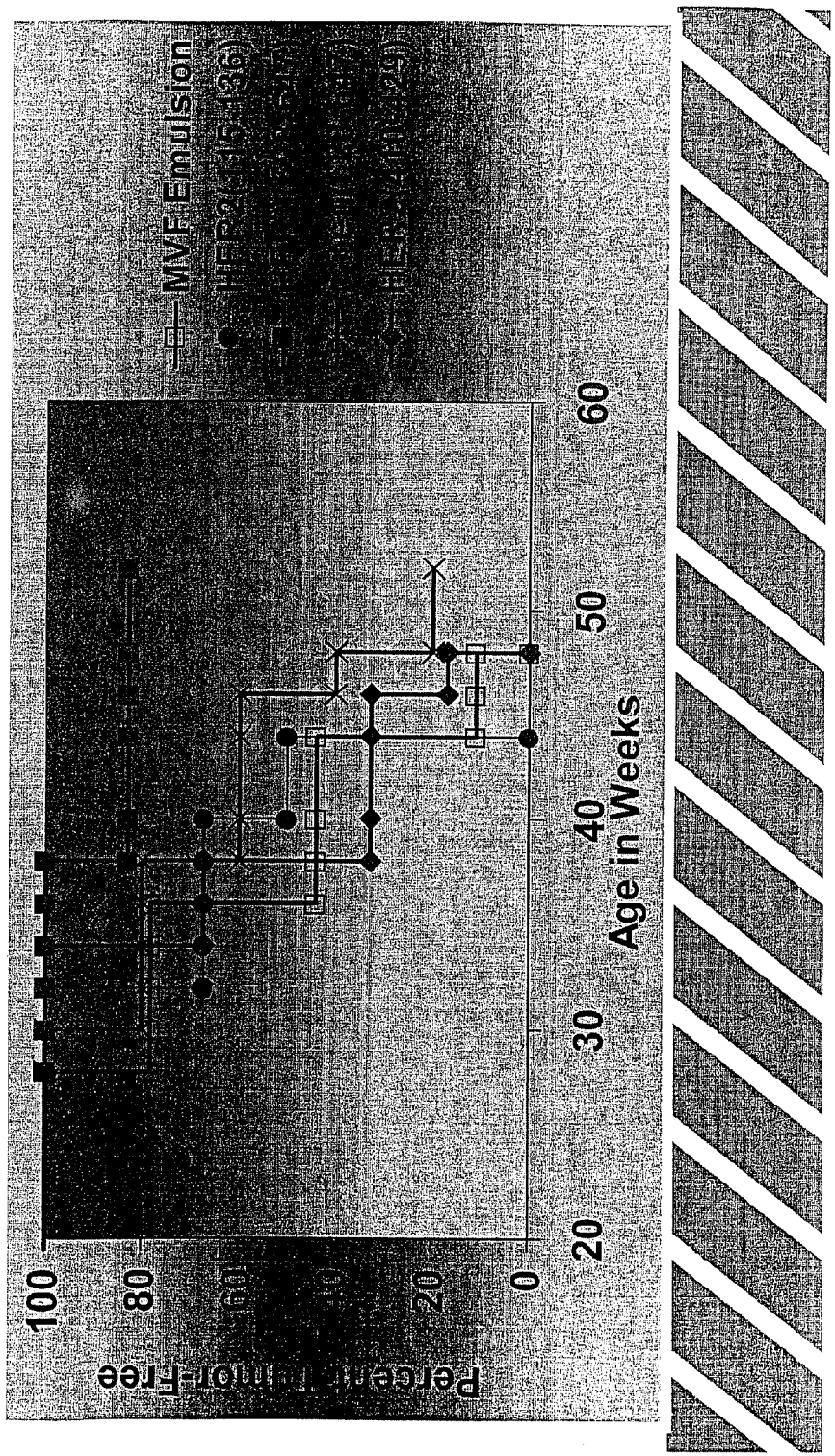
FIG. 8 shows the effect of vaccination with HER-2 B cell peptides on spontaneous breast tumor development. Groups of six mice were vaccinated with 100 µgs of peptides (pluse MDP as adjuvant emulsified in squalene arlacel A) around 4 weeks of age and boosted after 4, 8, 16, and 24 weeks. Tumors were calculated as length×width$^2$/2) The time to tumor development was analyzed using Kaplan-Meier survival analysis with log rank comparisons of individual curves.

FACS and Immunoprecipitatio: Flow cytometric analysis determined that DW1MVF anti-peptide antibody directly targeted the HER-2 receptor. (See FIG. 3) A commercially available mouse Mab to HER-2/neu was used as a control in SKBR3 cells. Negative control sera showed no binding to the receptor while an increase in fluorescence was seen with the immune sera. Fluorescence intensity of the polyclonal anti-peptide serum was comparable to the monoclonal antibody. Therefore polyclonal serum can mimic the specificity and affinity of monoclonal antibodies.

Immune serum was serially diluted in Hank's Balanced Salts Solution and the mean cell fluorescence determined. Serum from the 'tertiary+3 weeks' bleed gave a fluorescence value of 121.4 (diluted 1:320) while the MAb gave a value of 132. The following is a list of the mean cell fluorescence values at various serum dilutions.

| Dilution | Mean Cell Fluorescence (DWLMVF) |
|---|---|
| Control | 0.647 |
| 1:80 | 39.3 |
| 1:160 | 83.5 |
| 1:320 | 121.4 |
| 1:640 | 69.4 |
| 1:1280 | 34.4 |
| 1:2560 | 17.4 |

The peptide antibodies MVFDW4, DW5MVF and DW6MVF however did not give the same intensity of fluorescence as DW1MVF. Therefore, immunoprecipitation was used to verify specificity for HER-2. SKBR3 cells were immnunoprecipitated with Protein A/G purified antipeptide antibodies. Antibodies are shown to be HER-2 reactive v'. Identical bands are evident in the Mab sample and the anti-peptide antibodies.

Identification of the Biological Effects of Antipeptide Antibodies

Proliferation in vitro. Once specificity for HER-2 was confirmed the next step was to determine biological activity, in this case a reduction in tumor growth such as that produced by incubation of MAbs with HER-2 overexpressing cells. The in vitro effects of antibody on tumor cells was determined by a standard tritiated thymidine proliferation assay. Antibodies DW1MVF, MVFDW4 and DW5MVF were able to reduce proliferation of SKBR3 cells in vitro. MCF-7 cells expressing normal amounts of the receptor were not inhibited by the antibodies. In contrast, a commercial monoclonal antibody that reduces tyrosine phosphorylation and DW6MVF which also reduces phosphorylation in vitro, stimulated cell growth in SKBR3 cells. These results show that polyclonal antibodies can behave like monoclonals in that biological effect is dependent on the epitopes recognized. Additionally, it is interesting to note that the inhibitory antibodies had negligible effect on cells expressing normal amounts of HER-2 (MCF7). This is also reported for some monoclonals and is advantageous for therapy of breast cancer where minimal toxicity of normal cells is desired.

Proliferation in vivo. Three out of four antipeptide antibodies were successful at retarding tumor growth in a nude mouse model albeit to different extents. All instances of tumor reduction were not the result of a decrease in autophosphorylation. A summary of the results suggests that some antibodies (MVFDW4 and DW5MVF) may require host effector cells for maximum tumor suppression. A plot of tumor progression vs time shows decreasing tumor volume with antibodies DW1MVF, MVFDW4 and DW5MVF. DW6MVF seemed to have negligible effects on growth.

Identification of Cytotoxic T Cell (CTL) Epitopes

CTL Assay. Peptide DW1MVF (376-395) has an overlapping T cell epitope 391-399. We wished to test the efficacy of this epitope for incorporation into a HER-2 vaccine. Results showed that a specific CTL response could be raised to a HER-2 derived peptide. Cytotoxic T cells primed with HER-2 391-399 were able to specifically lyse autologous targets in a dose dependent manner. However, two in vitro re-stimulations were necessary to produce this result. In this study IL-2 was added to the culture medium. It is expected that immunization with a peptide containing both T helper and cytotoxic T cell sequences will boost the results.

Effects of MVF-HER-2 Peptide Constructs in Rat neu Transgenic Mice. A transgenic mouse model (designated N202) that expresses mammary tumors similar to human breast cancer, developed by Muller and co-workers, Guy, C. T., et al, Proc.Natl. Acad. Sci. USA, 89: 10578-82, 1992 was employed to test in vivo anti-tumor effects of the chimeric peptides. Focal mammary tumors arise in at least 50% of the female transgenic mice around 28 weeks of age due to over-expression of the rat neu gene under murine mammary tumor virus 3' long terminal repeat. Three of the HER-2 peptide sequences (376-395, 410-429 and 628-647) have greater than 80% homology to the analogous regions in rat neu. We first examined whether the antibodies raised to the HER-2 peptides were capable of recognizing the rat neu receptor as there was a 20% amino acid sequence disparity. Results showed that antibodies elicited with HER-2 sequences (115-136), (410-429) and (628-647) were able to immunoprecipitate the rat neu receptor from neu gene overexpressing DHFR-C8 fibroblast cell line.

Based on these results, female transgenic mice were immunized with MVF constructs of HER-2 sequences 115-136, 410-429 and 628-647 and MVF alone separately. MVF HER-2 (628-647) elicited high titered antibody responses against the immunogen of over 50,000 as early as two weeks after the second booster, the antibody titers reached more than 250,000 after the third booster. Antibodies against MVF HER 2 (628-647) also reacted with recombinant HER-2 ECD with titers over 10,000 and the intact-HER-2 and rat neu receptors of cells. The transgenic mice did not mount appreciable antibody responses against HER-2 immunogens, 115 -136 MVF and 410 -429 MVF.

By 48 weeks of age, all of the transgenic mice immunized with MVF emulsion, HER-2 (115-136) MVF and HER-2 (410-429) MVF developed tumors of at least 10 millimeters in size. Most notably, in correlation with the in vitro inhibition of tumor cell proliferation , 83% (5 out of 6) transgenic mice immunized with MVF HER-2 (628-647) were completely free of tumors. MVF HER-2 (628-647) vaccinated mice showed significantly longer tumor free interval compared to mice immunized with MVF emulsion (P=0.0025). Although there was a delay in the onset of tumors in MVF HER-2 (628-647) immunized mice compared to other groups there was no significant difference in the kinetics of tumor growth after their occurrence.

Antibody-mediated Cytotoxicity of Breast Tumor Cell lines. We found IgG1 (58%) and IgG2 (35%) to be the major isotypes in the transgenic mouse sera elicited by MVF HER-2 (628-647). We tested its potential to recruit peripheral blood mononuclear cells to lyse HER-2 overexpressing mammary tumor cell lines in an ADCC assay. Peptide antibodies elicited in transgenic mice by HER-2 (628-647) invoked lysis of two different human breast tumor cell antibodies, some recognizing denatured protein.

Example 7

HER-2 (27-45)

A chimeric peptide comprising amino acids 27-45 of the HER-2 protein, the promiscuous helper T cell epitope from measles virus fusion protein (amino acids 288-302) at the N-terminus, and a GPSL (SEQ ID NO: 20) linker (MVFDN1) was synthesized using procedures as described above in example 1.

Example 8

HER-2 (316-339)

A chimeric peptide comprising a modified sequence 316-339 of the HER-2 protein, the promiscuous helper T cell epitope from measles virus fusion protein (amino acids 288-302) at the N-terminus, and a GPSL (SEQ ID NO: 20) linker (MVFND2) was synthesized using procedures as described in example 1 above. HER-2 sequence 316-339 contains three cysteines at positions 331, 334 and 338. Using molecular modeling software (Hyperchem, Hypercube Inc, Ontario, Canada), we determined that residues 334 & 338 form energetically most stable cysteine-cysteine bond pair. Hence, during synthesis we substituted Cysteine 331 with Alanine to prevent interference with secondary structure formation and aggregation post synthesis.

TABLE 3

Summary of free energy in kcal · mol and gradient in kcal/(mol · Angstrom) for three cysteine bond pairs and corresponding alanine mutants after geometry optimization of HER-2B-cell epitope (Sequence, 316–339) PLHNQEVTAEDGTQRCEKCSKPCA) using Polak-Ribiere energy minimization algorithm.

| | Energy | Gradient |
|---|---|---|
| Cys—Cys Bond Pair | | |
| 331 Cys–Cys 334 | 138.71 | 2.06 |
| 331 Cys–Cys 338 | 16.23 | .40 |
| 334 Cys–Cys 338 | 11.42 | 1.91 |
| C—C Bond/Ala Mutant | | |
| 331 C–C 334/ Cys 338–> Ala 338 | (−) 16.33 | 0.05 |

TABLE 3-continued

Summary of free energy in kcal · mol and gradient in kcal/(mol · Angstrom) for three cysteine bond pairs and corresponding alanine mutants after geometry optimization of HER-2B-cell epitope (Sequence, 316–339) PLHNQEVTAEDGTQRCEKCSKPCA) using Polak-Ribiere energy minimization algorithm.

|  | Energy | Gradient |
| --- | --- | --- |
| 331 C–C 338<br>Cys 334–> Ala 334 | 106.5 | 1.7 |
| 334 C–C 338/<br>Cys 331–> Ala 331 | 229.5 | 1.17 |

The HER-2 (316-339) epitope was linked to the Th epitopes comprising sequences 580-589 and 947-967 tetanus toxoid, designated TT and TT3, respectively and sequence 288-302 of the measles fusion protein, designated MVF to provide three different chimeric HER-2 B cell peptides.

Example 9

HER-2 (485-503)

A chimeric peptide comprising a modified sequence 495-508 of the HER-2 protein, the promiscuous helper T cell epitope from measles virus fusion protein (amino acids 288-302) at the N-terminus, and a GPSL (SEQ ID NO: 20) linker (MVFND3) was synthesized using procedures as described in example 1 above. HER-2 sequence 495-508 is four residues short of an optimal B-cell epitope of approximately 17-18 residues spanning the 750 Angstrom$^2$ antigen binding site of an antibody. Hence, in order to extend this sequence to fit the antigen-binding pocket better, we looked at the scores assigned to adjacent sequences for their probability to form an antigenic epitope. Sequence 485-499 was assigned the highest score of all sequences analyzed in the HER-2 extracellular domain on Welling's antigenicity scale, this scale indicates the probability of a 5 residue sequence to form an antigenic epitope. This sequence also harbors a defined β-turn (Residues 488-491) and an α-helix (Residues 491-495). Therefore, we extended the originally proposed epitope 495-508 to include 485-499. Furthermore, we shortened the sequence 495-508 by five residues at the C-terminus to exclude the single cysteine at position 504 that could lead to aggregation of the peptide and make it difficult for purification and characterization. The four residues following cysteine do not form any defined secondary. This epitope was linked with the promiscuous T helper cell epitope TT at the C-terminus (See Table 4).

TABLE 4

HER-2 B-cell epitope chimeric constructs incorporating promiscuous helper T cell epitope from tetanus toxoid (TT 580-599) at the C-terminus and a GPSL (SEQ ID NO:20) linker joining the two epitopes. Also shown is the % homology of the HBR-2 B-cell epitope sequences with corresponding sequences in rat NEU. Note: Cys 331 –> Ala 331 change in the construct HER-2 (316-339) TT is underlined.

| Chimeric HER-2 B-Cell Epitope Constructs | % Homology with rat NEU |
| --- | --- |
| HER-2 (27-45)-TT:<br>NH$_2$TGTDMKLRLPASPETHLDM-GPSL-<br>NSVDDALINSTIYSYFPSV-COOH<br>(SEQ ID NO:42) | 100 |

TABLE 4-continued

HER-2 B-cell epitope chimeric constructs incorporating promiscuous helper T cell epitope from tetanus toxoid (TT 580-599) at the C-terminus and a GPSL (SEQ ID NO:20) linker joining the two epitopes. Also shown is the % homology of the HBR-2 B-cell epitope sequences with corresponding sequences in rat NEU. Note: Cys 331 –> Ala 331 change in the construct HER-2 (316-339) TT is underlined.

| Chimeric HER-2 B-Cell Epitope Constructs | % Homology with rat NEU |
| --- | --- |
| HER-2 (316-339) TT:<br>NH$_2$PLHNQEVTAEDGTQR<u>A</u>EKCSKPCA-<br>GPSL-NSVDDALINSTIYSYFPSV-COOH<br>(SEQ ID NO:43) | 88.5 |
| HER-2 (485-503)-TT:<br>NH$_2$LFRNPHQALLHTANRPEDE-GPSL<br>NSVDDALINSTIYSYFPSV-COOH<br>(SEQ ID NO:42) | 80 |

Example 10

HER-2 (605 -622)

A chimeric peptide comprising amino acids 605-622 of the HER-2 protein, the promiscuous helper T cell epitope from measles virus fusion protein (amino acids 288-302) at the N-terminus, and a GPSL (SEQ ID NO: 20) linker (MVFDN4) was synthesized using procedures as described above in example 1.

Immunogenicity of the Peptides of Examples 7-10

The chimeric HER-2 peptides of examples 7-10 elicited variable antibody responses in pairs of immunized out bred rabbits. The most immediate and high titered antibodies were elicited by MVF HER-2 (316-339). Lower antibody responses were mounted against the other three peptide constructs. Despite the relative differences in the antibody titers, the antibodies produced in response to immunization with each of the chimeric peptides were able to recognize the HER-2 receptor both by flow cytometry and immunprecipitation.

The effect of combinations of chimeric peptides on antibody production in out bred rabbits was also determined. The results demonstrated that the B-cell epitope constructs MWFND2, MWFND3 and MWFDW4 elicited high titered antibody response of over 50,000 when administered either as single immunogen or their conbination in pairs of outbred rabbits. These rabbits were first immunized with individual epitopes and two weeks after the fourth booster the same rabbits were cross-immunized first with one of the three epitopes and later with all three epitopes. The antibody response to the cross immunogen was as good or better than they were administered as single immunogens.

Anti-proliferative Effects of the Chimeric Peptides of Examples 7-10 on Breast Tumor Cell Lines Antibodies elicited against the higher ranking HER-2 peptide sequences 316-339 and 485-503 of HER-2 inhibited growth of two human breast tumor cell lines, SKBR-3 and BT-474. MVF HER-2 (316-339) antibodies inhibited the growth of SKBR-3 and BT-474 cell lines by about 35% and 15% relativie to untreated or isotype antibody treated cells. MVF HER-2 (485-503) antibodies inhibited the growth of SKBR-3 cells by 22% and BT-474 by 11%. Antibodies raised against the HER-2 peptides 27-45 and 605-622 had negligible effect on the growth of tumor cell lines and appeared to enhance the growth of BT-474 cells similar to the isotype control antibody. None of the antibodies raised against the chimeric peptides of examples 7-10 inhibited growth of another human breast tumor cell line, MCF-7, which expresses normal levels of HER-2.

Cells of the breast tumor cell line SK-BR3 were also treated with mixtures of various HER-2 peptide antibodies, each at a concentration of 0.1 mg/ml. Treatment with a plurality of the antibodies resulted in an additive growth inhibitory effect which was greater than the inhibitory effect of a single antibody. A mixture of three different growth inhibitory peptide antibodies prevented greater than 90% of the proliferation of SK-BR-3 cell relative to untreated cells. Cells of the breast tumor cell line BT474 were also treated with mixtures of various HER-2 peptide antibodies at concentrations of 266 µg/ml, 528 µg/nml, and 792 µg/ml.

Example 11

MVFDW4-Microsphere

MVFDW4, prepared as described above in example is loaded into microspheres as described below.

Microsphere Preparation

Preparation of the microspheres was carried out in a controlled temperature jacketed beaker with a Glas-col/G.K. Heller HST10 N Stir-Tester. Microsphere preparations utilized 75/25 poly(DL-lactide-co-glycolide)(PLGA) with an inherent viscosity of 0.58 dL/g at 120 mg/ml. The peptide/polymer solution was emulsified in mineral oil/cottonseed oil with Span 85 (sorbitan trioleate) as an emulsifier at 40° C. After one hour of stirring at 750 rpm, the oil-in-oil emulsion was filtered thorough a 0.45 µm membrane and washed several times with petroleum ether. The filter was placed in a conical tube, frozen in liquid nitrogen, and lyophilized for at least three days. Peptide loading was determined by amino acid analysis.

Microsphere morphology, surface characteristics, and size were observed using a Philips Electronics XL-30 FEG scanning electron microscope. Dry samples were sprayed onto a carbon conductive tabbed specimen mount (3.2 mm pin diameter, 12.7 mm table diameter) which was sputter-coated for 110 seconds in an argon atmosphere. The images were obtained using a secondary electron detector and an accelerating potential of 5 kV at a working distance of 10 mm. At least one hundred particles for each preparation were sized from electron micrographs obtained using a Philips Electronics XL-30 Field Emission Gun Scanning, Electron Microscope.

Peptide loading was determined by extracting the peptide from the microspheres using ethyl acetate. Microspheres were immersed in excess ethyl acetate and vortexed vigorously. The undissolved polymer and released peptide was spun down by 5 minutes of centrifugation. The supernatant was removed and the process repeated three more times. Excess ethyl acetate was removed by evaporation. Samples were reconstituted in 2% acetic acid and submitted for amino acid analysis. The peptide was hydrolyzed in 6 N HCl and the subsequent amino acids derivatized and analyzed as their phenylthiohydantoins using a Waters PicoTag System, Peptide Immunization 100 µg of peptide and 100 µg of nor MDP in PBS is emulsified in 4:1 squalene:Arlacel and injected subcutaneously in multiple sites of five mice/peptide. Three weeks later, mice are boosted using the same protocol. Two weeks after the second immunization, spleens are recovered surgically.

Microsphere-encapsulated Peptide Immunization

MVFDW4 peptides and Nor-MDP adjuvant were individually encapsulated into microspheres 5.2% loading (MVFDW4), and 5% loading Nor-MDP. Microspheres that contain 100 µg peptide/mouse and 100 µg Nor-MDP/mouse were mixed with 200 µl of 4:1 squalene:Arlacel A and subcutaneously injected into mice.

Detection of CTL Activity

Two weeks after the last injection, splenocytes were taken from each mouse. Single cell suspension was prepared, part of which was used in INF-γ detection by Elispot, the rest for chromium-release assay.

(i) Elispot assay

A four-day Elispot protocol was used to detect the INF-γ production of spleen cells. On day 1, Elispot plate (PolyFiltronics) was coated with Anti-mouse-INF-γ (clone R4-6A2, Pharmingen) diluted in sterile PBS with no azide at 4 µg/ml. The plate was then incubated overnight at 4° C. in a humidity chamber. On day 2, the plate was washed with PBS four times and then blocked with 1% BSA in DMEM with no additives at 200 µl/well for 1 hour at room temperature. After BSA was removed, fresh spleen cells harvested into HL-1 medium (Biowhittaker) with 1% L-glutamine were added to wells at a certain concentration. The plate was then incubated in humidified incubator at 37° C., 5% $CO_2$ for 24 hours. On day 3, after cells were removed and plate washed with PBS once, the plate was further washed with PBS/Tween 20 (2000:1) four times. Biotinylated anti-INF-γ (clone XMG 1.2, Pharmingen) diluted in PBS/Tween 20/1% BSA to 2 µg/ml was added into wells at 100µl/well. The plate was incubated at 4° C. overnight in a humidity chamber. On day 4, after the plate was washed with PBS/Tween 20 four times, goat anti-biotin/alkaline phosphatase conjugate(Vector Laboratories Inc.) 1:1000 diluted in PBS/Tween 20/1% BSA was added at 100 µl/well. The plate was incubated at room temperature for 2 hours, washed with PBS four times. BCIP/NBT alkaline phosphatase substrate(Kirkegaard and Perry Laboratories Inc.) was added at 200 µl/well for incubation at room temperature. The reaction was quenched in running tap water when spots were visualized on the plate. The plates were air dried prior to reading the spots.

(ii) Cytotoxic lysis assay

In vitro re-stimulation was performed using syngeneic spleen cell stimulators, which were taken from the same batch of single cell suspension and pulsed for 1 h with the p63 synthetic peptide. Responder cells: stimulator cells (3:1) were mixed in 24-well late and incubated at 37° C. for a week and then those responder splenocytes was used as the effector cells in the following CTL assay. CTL assay was performed using standard Chromiun release assay. Briefly, peptide-pulsed targets were prepared by incubating the SVBalb cells ($H-2^d$) or MCS7 cells($H-2^b$, as control) with or without 10 µg/ml of peptide p63 and 500 µCi/ml of $^{51}$Cr sodium chromate for 1 h at 37° C. Labeled target cells ($10^4$ cells/well) and various numbers of effector cells were plated in a final volume of 0.2 ml in 96-well plate. After 5 hours at 37° C., 50 µl of supernatant was collected from each well, and percent specific lysis was determined according to the formula: [(cpm of the tested sample—cpm of the spontaneous $^{51}$Cr release) / (cpm of the maximal $^{51}$Cr release-cpm of the spontaneous $^{51}$Cr release)] ×100.

Example 12

HER-2 is extensively glycosylated at seven potential sites in the extracellular domain alone. We have identified B-cell epitopes that harbor these N-linked glycosylation sites (Asn-X-Ser/Thr-X) by computer aided analysis. Three constructs comprising B-cell epitope encoding sequences suitably mutated to improve glycosylation and their wild type counterparts HER-2 (115-136); (182-216); and (630-650) and T helper cell epitope are subcloned into a baculovirus mammalian shuttle expression vector. This vector allows easy baculovirus virus mediated transfection of gene of interest into mammalian cells, but cannot replicate in the cells allowing efficient expression and glycosylation of the epitopes. The expressed chimeric glycosylated epitopes are characterized by capillary electrophoresis for the type of sugars and glycosylation efficiency. Rabbits are immunized with efficiently glycosylated epitopes and peptide antibodies generated.

The invention now being fully described, it will be apparent to one of ordinary skill in the art that many changes and modifications can be made thereto without departing from the spirit or scope of the appended claims.

What is claimed is:

1. A chimeric peptide composition for stimulating an immune response to HER-2 protein, wherein said chimeric peptide comprises: a HER-2 B cell epitope, a T helper (Th) epitope, and a linker joining said HER-2 B cell epitope to said Th epitope, wherein:
   the HER-2 B cell epitope consists of KPDLSYMPIWKF-PDEEGA, SEQ ID NO: 11;
   the Th epitope comprises a sequence selected from the group consisting of:
   NSVDDALINSTIYSYFPSV, SEQ ID NO: 13;
   PGINGKAIHLVNNQSSE, SEQ ID NO: 14;
   QYIKANSKFIGITEL, SEQ ID NO: 15;
   FNNFTVSFWLRVPKVSASHLE, SEQ ID NO: 16;
   LSEIKGVIVHRLEGV, SEQ ID NO: 17;
   FFLLTRILTIPQSLN, SEQ ID NO: 18; and
   TCGVGVRVRSRVNAANKKPE, SEQ ID NO: 19; and
   the linker is from 1 to 15 amino acids in length.

2. The chimeric peptide of claim 1 wherein said linker is from 2 to 15 amino acids in length.

3. The chimeric peptide of claim 1 wherein the Th epitope comprises LSEIKGVIVHRLEGV, SEQ ID NO: 17.

4. The chimeric peptide of claim 1 wherein the linker comprises the sequence GPSL, SEQ ID NO: 20.

5. The chimeric peptide of claim 1 further comprising a second HER-2 B cell epitope comprising an amino acid sequence selected from the group consisting of:
TGTDMKLRLPASPETHLDM, SEQ ID NO: 1:
AVLDNGDPLNNTTPVTGASPGG, SEQ ID NO: 2:
LWKDIFHKNNQLALTLIDTNRS, SEQ ID NO: 3:
TLIDTNRSRACHPCSPMCKGSRCWGESSEDCQSLT, SEQ ID NO: 4:
ALVTYNTDTFESMPNPEGRYT, SEQ ID NO: 5:
PLHNQEVTAEDGTQRAEKCSKPCA, SEQ ID NO: 6:
PESFDGDPASNTAPLQPE, SEQ ID NO: 7:
LYISAWPDSLPDLSVFQNLQ, SEQ ID NO: 8:
LFRNPHQALLHTANRPEDE, SEQ ID NO: 9:
CLPCHPECQPQNGSVTCFGPEADQCVACAHYKDP, SEQ ID NO: 10:
KPDLSYMPIWKFPDEEGA, SEQ ID NO: 11: and
INGTHSCVDLDDKGCPAEQRAS, SEQ ID NO: 12.

6. A method of stimulating an immune response in a subject comprising administering a pharmaceutical composition to said subject, said pharmaceutical composition comprising:
   the chimeric peptide of claim 1, and
   a pharmaceutically acceptable vehicle.

7. The method of claim 6 wherein the subject is a human and has one of the following cancers or a predisposition to one of the following cancers: breast cancer, ovarian cancer, lung cancer, prostate cancer, and colon cancer.

8. The method of claim 6 wherein the vehicle is biodegradable and is selected from the group consisting of an emulsion comprising a pharmaceutically acceptable oil/water emulsion and a biodegradable microsphere or nanosphere comprising a polylactide-polyglycolic acid polymer.

9. The method of claim 8 wherein the oil is squalene or squalane.

10. The method of claim 8 wherein the microsphere is from 0.1 to 50 nanometers in diameter and comprises poly(D,L lactide-co-glycide).

11. The chimeric peptide of claim 5, further comprising a second linker joining the first HER-2 B cell epitope to the second HER-2 B cell epitope.

12. The chimeric peptide of claim 11, wherein the second linker is from 1 to 15 amino acids in length.

13. The chimeric peptide of claim 12, wherein the second linker comprises the sequence GPSL, SEQ ID NO: 20.

14. The chimeric peptide of claim 1 wherein the Th epitope comprises NSVDDALINSTIYSYFPSV, SEQ ID NO: 13.

15. The chimeric peptide of claim 1 wherein the Th epitope comprises PGINGKAIHLVNNQSSE, SEQ ID NO: 14.

16. The chimeric peptide of claim 1 wherein the Th epitope comprises QYIKANSKFIGITEL, SEQ ID NO: 15.

17. The chimeric peptide of claim 1 wherein the Th epitope comprises FNNFTVSFWLRVPKVSASHLE, SEQ ID NO: 16.

18. The chimeric peptide of claim 1 wherein the Th epitope comprises FFLLTRILTIPQSLN, SEQ ID NO: 18.

19. The chimeric peptide of claim 1 wherein the Th epitope comprises TCGVGVRVRSRVNAANKKPE, SEQ ID NO: 19.

* * * * *